(12) United States Patent
Mellem

(10) Patent No.: US 11,559,698 B2
(45) Date of Patent: Jan. 24, 2023

(54) SYSTEM FOR INDUCING AN ELECTRIC FIELD IN A CONDUCTING MEDIUM, ESPECIALLY FOR MEDICAL APPLICATIONS

(71) Applicant: Krzysztof Mellem, Jelenia Gora (PL)

(72) Inventor: Krzysztof Mellem, Jelenia Gora (PL)

( * ) Notice: Subject to any disclaimer, the term of this patent is extended or adjusted under 35 U.S.C. 154(b) by 0 days.

(21) Appl. No.: 17/268,537

(22) PCT Filed: Sep. 1, 2019

(86) PCT No.: PCT/PL2019/050048
§ 371 (c)(1),
(2) Date: Feb. 15, 2021

(87) PCT Pub. No.: WO2020/050730
PCT Pub. Date: Mar. 12, 2020

(65) Prior Publication Data
US 2021/0308478 A1    Oct. 7, 2021

(30) Foreign Application Priority Data
Sep. 3, 2018 (PL) .......................... 426887

(51) Int. Cl.
*A61N 2/00* (2006.01)
*A61N 2/02* (2006.01)

(52) U.S. Cl.
CPC ............. *A61N 2/008* (2013.01); *A61N 2/006* (2013.01); *A61N 2/02* (2013.01)

(58) Field of Classification Search
CPC ........... A61N 2/006; A61N 2/008; A61N 2/02
See application file for complete search history.

(56) References Cited

U.S. PATENT DOCUMENTS

| 9,233,258 B2 | 1/2016 | Simon et al. |
| 2011/0125203 A1 | 5/2011 | Simon et al. |
| (Continued) | | |

FOREIGN PATENT DOCUMENTS

| PL | 206581 B1 | 3/2007 |
| WO | 2001/007111 A2 | 2/2001 |
| WO | 2002/062283 A2 | 8/2002 |

OTHER PUBLICATIONS

Maass, J. and Asa, M., 1970. Contactless nerve stimulation and signal detection by inductive transducer. IEEE Transactions on Magnetics, 6(2), pp. 322-326.

(Continued)

*Primary Examiner* — Christine H Matthews

(57) ABSTRACT

The subject of the invention is a system for inducing an electric field in a conducting medium, especially for medical applications. The system according to the invention induces a flow of electric current through objects located in the conducting medium, which may have shapes that are complex or change with time, and has a medical application consisting in a complete or partial nerve impulse block. The system for inducing an electric field in the conducting medium comprises at least two component cores, whose magnetization is configured to be changed independently by a change of electric currents flowing through windings that are wound around them, and a torus-shaped encasement whose outer surface is electrically non-conductive, wherein the component cores are situated inside the encasement and encircle its opening, and the encasement is situated inside the conducting medium.

21 Claims, 7 Drawing Sheets

(56) References Cited

U.S. PATENT DOCUMENTS

2016/0361540 A9* 12/2016 Simon .................. A61N 1/40
2018/0193658 A1* 7/2018 Hong .................. A61N 2/006

OTHER PUBLICATIONS

Ueno, S., Harada, K., Ji, C. and Oomura, Y., 1984. Magnetic nerve stimulation without interlinkage between nerve and magnetic flux. IEEE Transactions on Magnetics, 20(5), pp. 1660-1662.

* cited by examiner

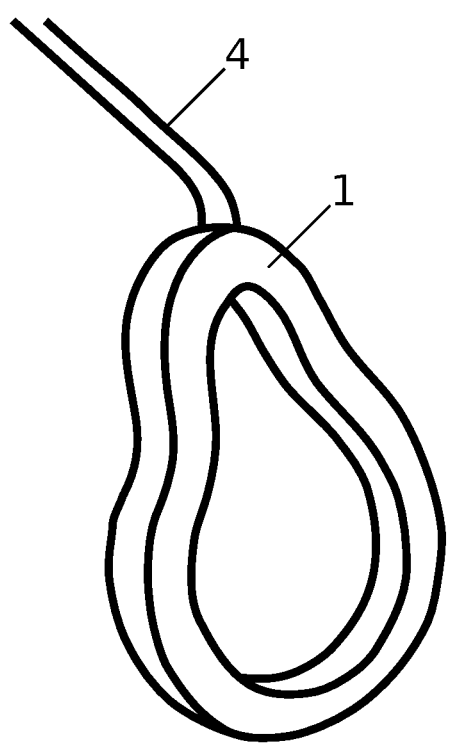
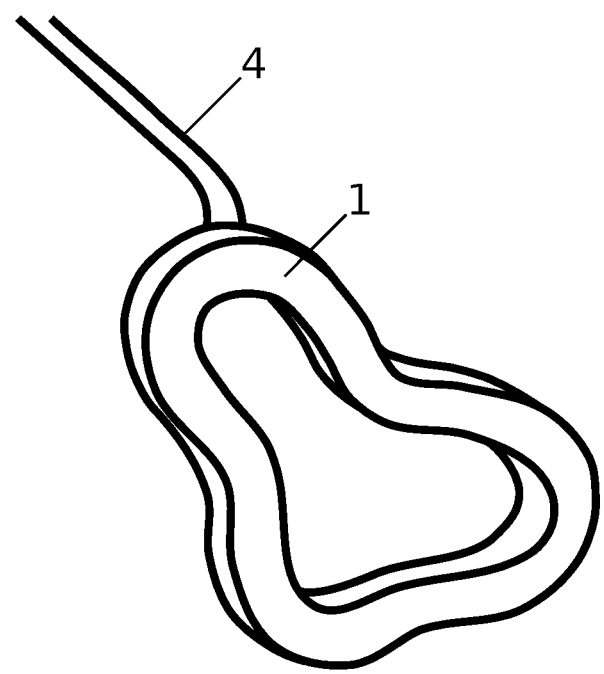
Fig. 3a  Fig. 3b
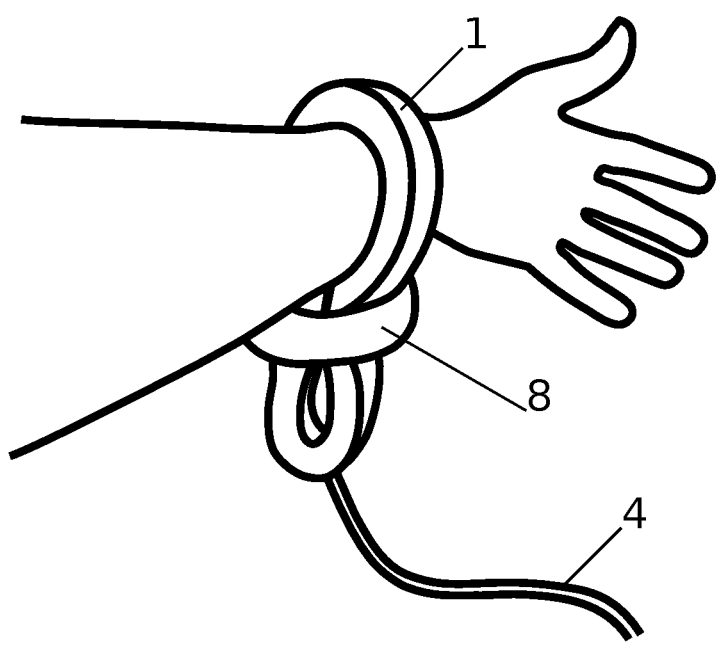
Fig. 4

SYSTEM FOR INDUCING AN ELECTRIC FIELD IN A CONDUCTING MEDIUM, ESPECIALLY FOR MEDICAL APPLICATIONS

RELATED APPLICATIONS

This application is a National Stage Entry of International Application No. PCT/PL2019/050048, filed Sep. 1, 2019, which claims priority to Polish Patent Application No. PL426887, filed Sep. 3, 2018, the contents of all of which are incorporated herein by reference, in their entirety.

FIELD OF THE INVENTION

The subject of the invention is a system for inducing an electric field in a conducting medium, especially for medical applications. The system according to the invention induces a flow of electric current through objects placed in the conducting medium, which can have shapes that are complex or change with time, and has a medical application consisting in a complete or partial nerve impulse block, thus providing a partial or complete blockage of the movement as well as a reduction of intensity or a complete disappearance of the sensory stimuli felt by the patient, including the feeling of pain.

BACKGROUND OF THE INVENTION

There are known systems that generate electric field utilizing the phenomenon of electromagnetic induction described by Faraday's law. Systems utilizing magnetic cores immersed in a medium with a good electrical conductivity enable to obtain high electric field intensity using significantly smaller current than in the case of systems utilizing air core coils. This is a result of much higher magnetic permeability of the materials the magnetic cores are made from, so that a small changing current, which flows through windings that surround them, allows to obtain a high changing magnetization of the core, thus creating a large electromotive force by the means of a high changing magnetic flux.

The possibility of a complete or partial nerve impulse block utilizing electrodes is known in the scientific field for a long time. Thus far it was not widely used outside the laboratory due to necessity for utilizing large currents that are generated continuously, which results in electrochemical reactions on the surface of electrodes that are harmful for the human body.

The publication "Contactless nerve stimulation and signal detection by inductive transducer", Maass, J., M. Asa, describes the use of an electric field induced by a magnetic core in order to elicit an action potential in a nerve in vivo. A magnetic core consisted of two halves that were covered with a medical-grade-silicon rubber, which allowed to put the core on a nerve fiber that constituted a secondary winding of the transformer. The publication does not mention a possibility of utilizing the silicone coat to provide a tight contact between the core and the nerve fiber, and the description as well as the drawings show that the nerve fiber should have an ability to move freely relative to the core.

The article "Magnetic nerve stimulation without interlinkage between nerve and magnetic flux", Ueno, S., et al., describes a magnetic core inducing an electric field in a conducting medium, which is surrounded by an insulating cover that enables shaping of the current flow. The cover may have an arbitrary, pre-determined shape. The article does not mention a possibility of using a cover made from an elastic material, which would decrease losses caused by a current not going into the nerve fiber by the means of a tight contact.

In patent literature the application WO 2001007111 describes a use of a system utilizing a magnetic core in order to transcutaneously elicit an action potential in patient's body by the means of an electric field induced by a magnetic core in a vessel filled with a conductive fluid. The application does not mention a possibility of utilizing the system to block nerve impulses. The cores may have various, pre-determined shapes and are covered with a non-conductive coat made from a stiff epoxy paste.

In U.S. Pat. No. 9,233,258 the patent description shows a system for generating an electric field by the means of magnetic cores situated in a cover comprising a conducting medium, in which a good electrical contact with the body is provided by filling with the conducting medium or by the means of an elastic membrane having a good electrical conductivity, through which an induced current flows. One of the variants describes a thin membrane of high dielectric constant, which acts as a conductor for capacitive currents of high frequency. The applied solutions allow only for affecting a small surface area and the patent description does not suggest utilizing deformable, electrically non-conductive elastomers, that would create a barrier for the current flow.

A magnetic coil intended for utilization in textile products, with a winding made from a conducting yarn and a core made from a fiber that contains a magnetic powder, which posses an ability to change its shape that is appropriate for textile products is known from patent description PL 206581. This system is, however, unsuitable for inducing and shaping an electric field in a conducting medium.

SUMMARY OF THE INVENTION

The purpose of the present invention is a system for inducing an electric field in a conducting medium characterized by an ability to affect objects which may have shapes that are complex or change with time by an electric field in such a way that as much as possible of the induced current goes into the object that is affected.

Another purpose of the present invention is a system for inducing a high electric field intensity in a conducting medium by the means of a low voltage.

Further purpose of the present invention is a system for inducing an electric field capable of a complete or partial block of action potential in motor and sensory nerves in order to increase patient's comfort by providing analgesia or anesthesia, characterized by safety features allowing for an unassisted therapy. The system according to the invention may be also utilized to provide analgesia or anesthesia as an implant inside the patient's body.

In the further part of the description a system comprising at least two magnetic cores encompassed by an electrically non-conductive encasement will be called a complex core. The term core should be understood as a magnetic core or a magnetic circuit, which in certain variants may comprise branches. Component cores are independent magnetic circuits with separate windings and their magnetization may be distinguished by a different time course. The property of being electrically non-conductive should be interpreted in relation to the electrically conductive elements of the system according to the invention, wherein in the preferred embodiment the ratio of resistivities of these elements is higher than 100, in a more preferred embodiment higher than 10000, and in the most preferred embodiment higher than 1000000. The outer surface of the encasement should be understood as the surface that would be in contact with a conducting medium if the encasement was fully immersed in the conducting medium in the form of a fluid. In the preferred embodiment the outer surface of the encasement, inside which the component cores are situated, is shaped like a torus, and the encasement is torus-shaped. This should be understood in a broad sense, in particular a torus may also mean objects that are topologically equivalent to a torus. For example, the encasement may have a variable cross section and may be nonaxisymmetric. The electrically non-conductive outer surface of the encasement shapes the flow of the current that is induced by the component cores in the conducting medium in such a way, that the induced current flows around the encasement approximately tangentially to its outer surface. The complex core and the encasement have collectively at least one opening, which is also called an inner opening, that provides a continuous flow of the induced current in the conducting medium, wherein in the preferred embodiment there is only one inner opening, through which all of the induced current flows. In the preferred embodiment the component cores are shaped like a torus or a toroid and encircle the inner opening of the encasement, so that the induced current in the conducting medium flows around the encasement through its inner opening. An electric field shaping element is an electrically non-conductive solid, that is connected to the complex core in such a way, that all of the induced current that flows through the inner opening of the complex core flows into the inside of the electric field shaping element, after which it flows outside through its openings. A membrane is a limp sheet of an electrically non-conductive material, which is connected to the complex core in such a way, that all of the induced current that flows through the inner opening of the complex core flows into the inside of the membrane, after which it flows outside through its openings. If a variant of the present invention utilizes a complex core it should be recognized that a variant utilizing instead a single core encompassed by an encasement is also possible. The current induced by the component cores of the complex core may be referred to as the induced current of the complex core. The term time course, when not used in a specific context, refers to a time course or a waveform of the induced electromotive force along a loop that passes through the opening of the encasement and encircles it inside the conducting medium. An object or a group of objects, which are electrically conductive and are situated inside the conducting medium, are affected by the system according to the invention when the current induced by the component cores in the conducting medium flows through them. In the further part of the description this phenomenon is referred to briefly as affecting the object, and the area in which it takes place is called the area of affection. A conducting medium is any electrically conductive matter, wherein in the preferred embodiment it is a solid or a liquid whose electrical conductivity is higher than the electrical conductivity of the object that is affected in order to decrease ohmic losses. For example, the conducting medium may be any electrolyte or a human body, in case of a complex core acting as an implant. All variants of a system according to the present invention may be utilized for affecting human and animal body as well as any other object, including the animate and inanimate matter.

The invention provides a system for inducing an electric field in a conducting medium by a change of magnetization of cores placed in it caused by a change of current flowing through windings that surround them, characterized in that an outer surface of an electrically non-conductive encasement, capable of a reversible change of shape due to contact with an object placed in the conducting medium by strength of hands, is a torus inside which at least two component cores are situated.

The invention also provides a system for inducing an electric field in a conducting medium, comprising at least two component cores, whose magnetization is configured to be changed independently by a change of electric currents flowing through windings that are wound around them, and a torus-shaped encasement, whose outer surface is electrically non-conductive, wherein the component cores are situated inside the encasement, the component cores encircle an opening of the encasement and the encasement is situated inside the conducting medium.

Preferably, at least a portion of the outer surface of the encasement is capable of a reversible change of shape by strength of hands.

Preferably, the encasement comprises at least one seal having an ability of bending by strength of hands.

Preferably, the component cores have an ability of reversible change of shape by strength of hands.

Preferably, the encasement is tightly and separably connected to an electrically non-conductive electric field shaping element.

Preferably, the encasement is tightly and separably connected to an electrically non-conductive membrane.

Preferably, the highest voltage of wires is lower than 12 V, in a more preferred embodiment lower than 10 V, in an even more preferred embodiment lower than 5 V and in the most preferred embodiment lower than 3 V.

Preferably, an energy source of a power-control system is an electric battery.

Preferably, the windings of at least two component cores are connected in parallel.

Preferably, at least two component cores reach saturation magnetization at the same time.

Preferably, electromotive forces induced by at least two component cores are distinguished by a different time course.

Preferably, the encasement and a cable form together with the power-control system by the means of tight connections an ensemble that is completely electrically insulated from the conducting medium.

Preferably, the encasement has at least one chamber filled with a solid body or a fluid with a density smaller than the density of the conducting medium.

BRIEF DESCRIPTION OF THE DRAWINGS

The invention is explained in an exemplary embodiment presented in figures, where FIG. 3a and FIG. 3b show a change of shape of an elastic complex core, FIG. 4 shows an elastic complex core put on an arm.

DETAILED DESCRIPTION

Figure 1:
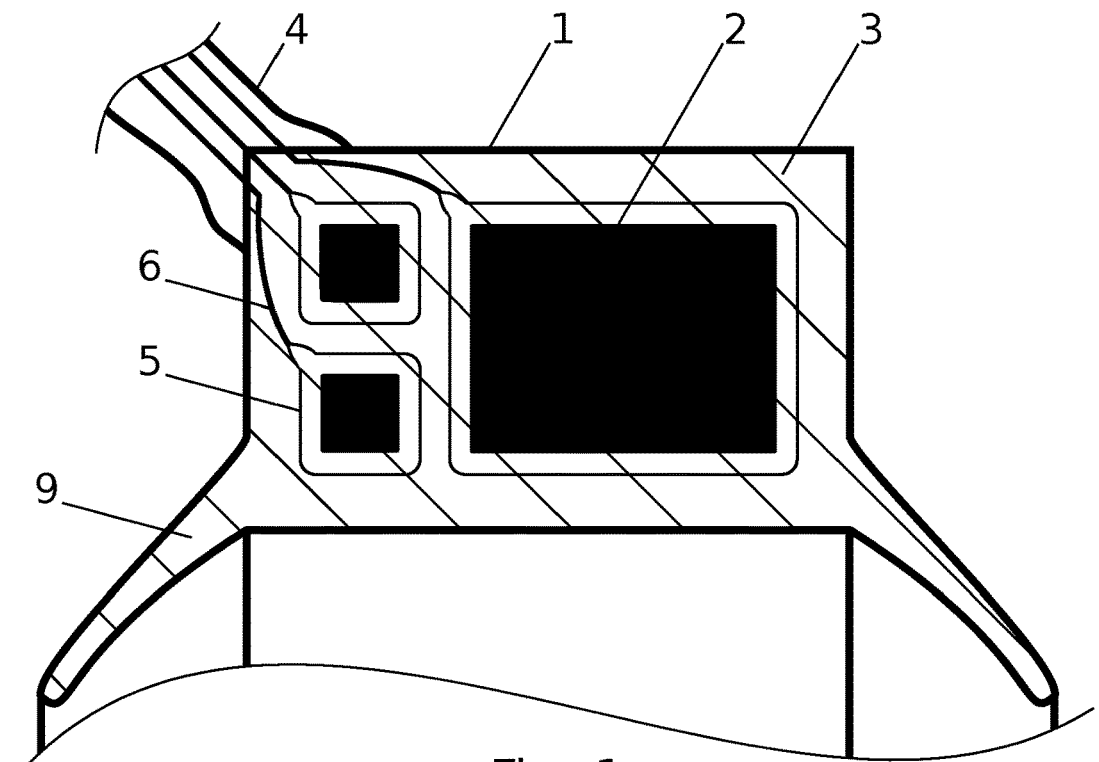
FIG. 1 shows a complex core in a partial cross section.

A system for inducing an electric field, as shown in FIG. 1, is a complex core 1 that is furnished with three component cores 2, which are placed along radius and axis of the complex core inside an electrically non-conductive encasement 3, whose outer surface is shaped like a torus and has an ability of reversible change of shape by a small force in order to provide a tight contact with an object that is affected by the electric field. The component cores 2 are independent magnetic circuits shaped like a torus. The encasement 3 comprises a seal 9 having an ability of bending by a small force. Windings 5 of each of the component cores 2 are powered independently by wires 6 that are located inside a cable 4. For this reason, the magnetization of each component core 2 may be changed individually by the means of a changing current flowing through the winding 5 that is wound around it. Each winding 5 may comprise different number of turns, and in the preferred embodiment the wire 6 is twisted in order to reduce the parasitic inductance. The complex core 1 induces flow of the electric current in the conducting medium in agreement with the Faraday's law, as a result of a change of magnetization of the component cores 2 caused by a change of current flowing through the windings 5 and wires 6. Initially, the induced electric field vector may have a component that is perpendicular to the outer surface of the encasement 3 or the seal 9, although due to the fact that their surfaces are electrically non-conductive, as a result of the flow of the induced current through the conducting medium some electric charges are quickly embedded on said surfaces, thus creating an electric field that directs the induced current approximately tangentially to these surfaces. Due to the small capacitance of the encasement 3 and the seal 9 these electric charges are usually of negligible value, and the shaping of the flow of the induced current usually occurs after a negligible amount of time.

Figures 2A, 2B:
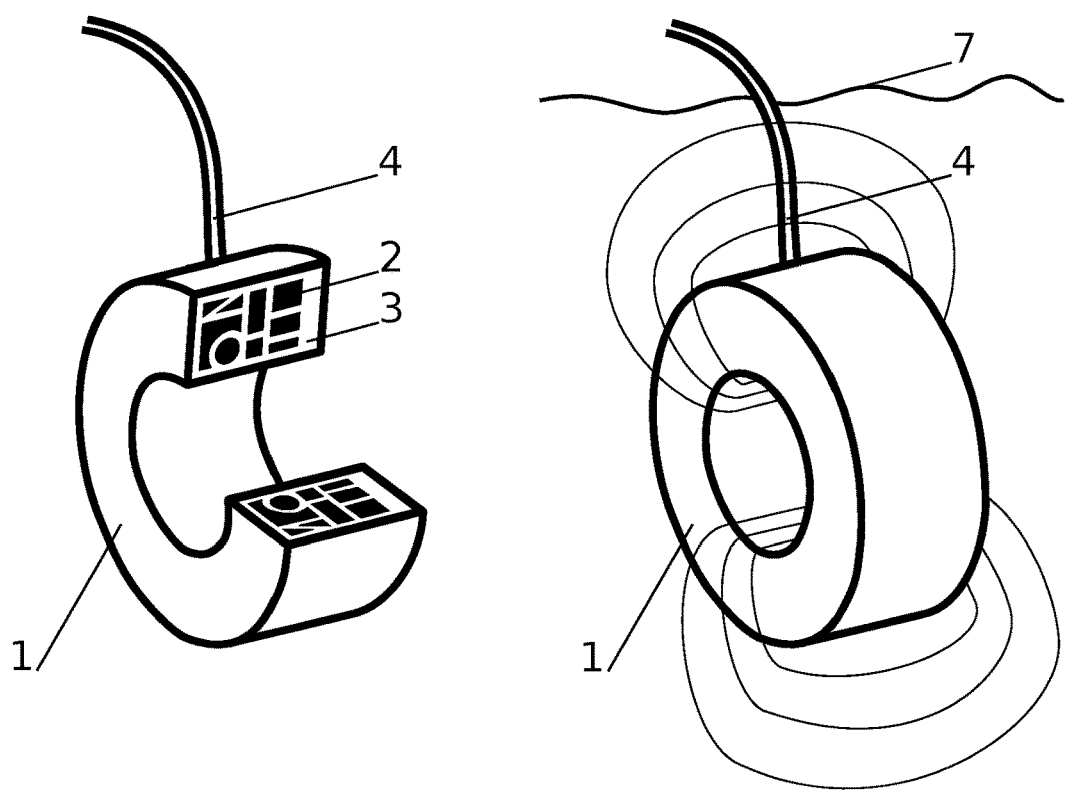
FIG. 2a shows a complex core in an offset section.
FIG. 2b shows a complex core immersed in a conducting medium, with visible electric field lines.

In the embodiment shown in FIG. 2a the complex core 1 comprises independent component cores 2 of various shapes, that are encompassed by the encasement 3, which prevents movement between the closely packed cores. The interior of the torus-shaped encasement 3 that surrounds the component cores 2 is an electrically non-conductive solid. The component cores 2, which encircle the opening of the encasement, are separate toroids with a common axis of rotation. Electric current, which is provided independently to the windings of the component cores 2, is supplied by the cable 4.

A system for inducing an electric field according to the invention is shown in FIG. 2b, which reveals part of the electric field lines that are induced by the complex core 1 immersed in a conducting medium 7. In case of an electrically homogeneous medium the electric field lines may be equated to the electric current lines, which flow around the electrically non-conductive encasement creating closed loops.

In the embodiment shown in FIG. 3a and FIG. 3b, a reversible change of shape of an elastic complex core 1 is depicted in two positions. In this variant, the elastic core may be also made in the form of a single elastic core that is encompassed by the encasement.

In the embodiment shown in FIG. 4 the elastic complex core 1 was put on an arm by the means of a clamp 8, which allows for a tight fit between the core and the forearm and holds it in place. In this case the object that is affected is the arm and more broadly the tissues of the body, for example the skin, the adipose tissue, the nervous tissue and others.

Figure 5A:
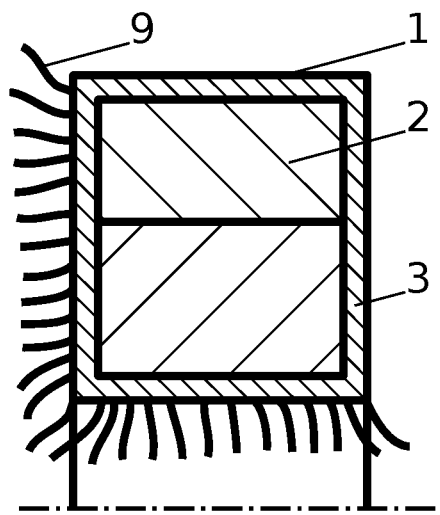
FIG. 5a shows a complex core comprising two cores connected in parallel, which reach saturation magnetization at the same time, furnished with a seal in the form of densely packed, limp rods, in a half-section.

In the embodiment shown in FIG. 5a the complex core 1 comprises two component cores 2, each of them wound with a single turn, whose dimensions were chosen in such a way, that they reach saturation magnetization at the same time when powered in parallel. The torus-shaped component cores 2 are separate toroids that surround the opening of the complex core 1. The encasement 3 comprises the seal 9 in the form of densely packed, limp rods made from an elastomer. The seal 9 allows for a tight contact in case of a core that is put on the body and in case of a core that is put near the surface of the body.

Figure 5B:
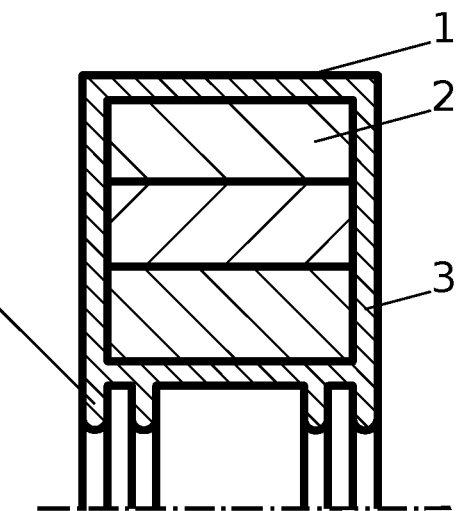
FIG. 5b shows a complex core with a seal, comprising three cores connected in parallel, which reach saturation magnetization at the same time, in a half-section.

In the embodiment shown in FIG. 5b the complex core 1 comprises three component cores 2, each of them wound with a single turn, whose dimensions were chosen in such a way, that they reach saturation magnetization at the same time when the windings are connected in parallel. The component cores 2 are separate toroids that surround the opening of the complex core 1. The encasement 3 comprises the seal 9 in the form of double lip seals, which are placed from both sides of the complex core 1.

Figure 6:
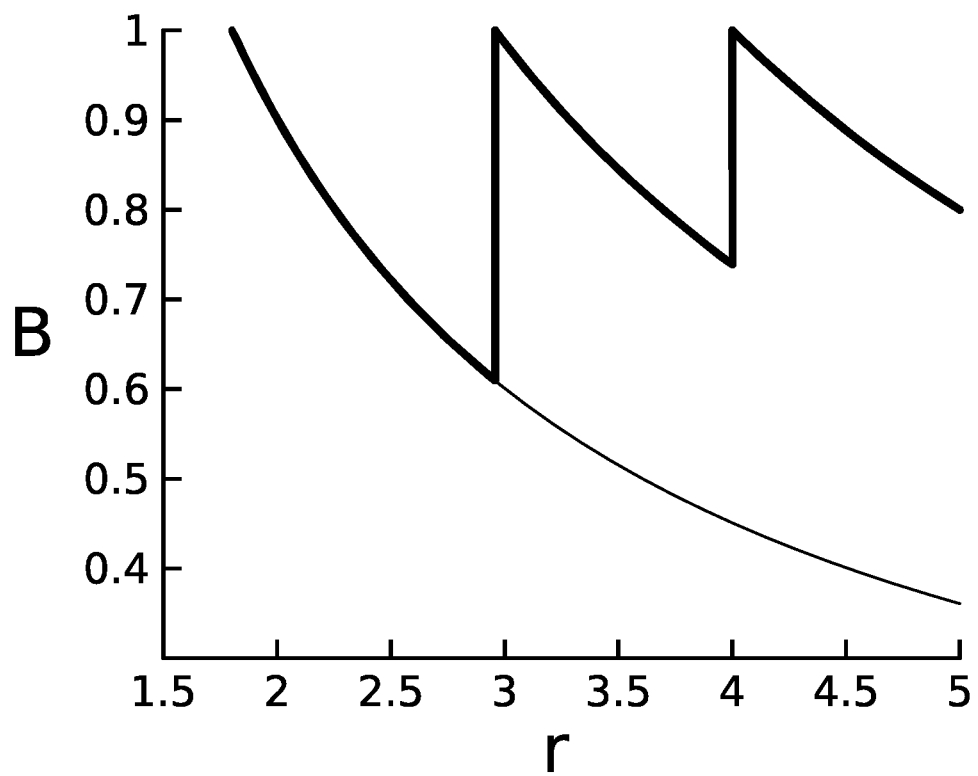
FIG. 6 shows a graph comparing a change of value of magnetic flux density along the radius of a complex core from FIG. 5b and along the radius of a single core having the same dimensions.

The FIG. 6 features a graph comparing a change of value of magnetic flux density along the radius of a complex core from FIG. 5b, which is represented on the graph with a thick line, and along the radius of a single core having the same inner and outer radius, that is represented on the graph with a thin line. The value of the magnetic flux density B presented on the vertical axis and the distance from the axis of the core r depicted on the horizontal axis were expressed in arbitrary units. The comparison reveals that the use of the complex core 1 allows to obtain much larger magnetic flux with the same dimensions of the system, which amounts to a significantly greater value of induced electric field intensity in a unit of time.

Figure 7:
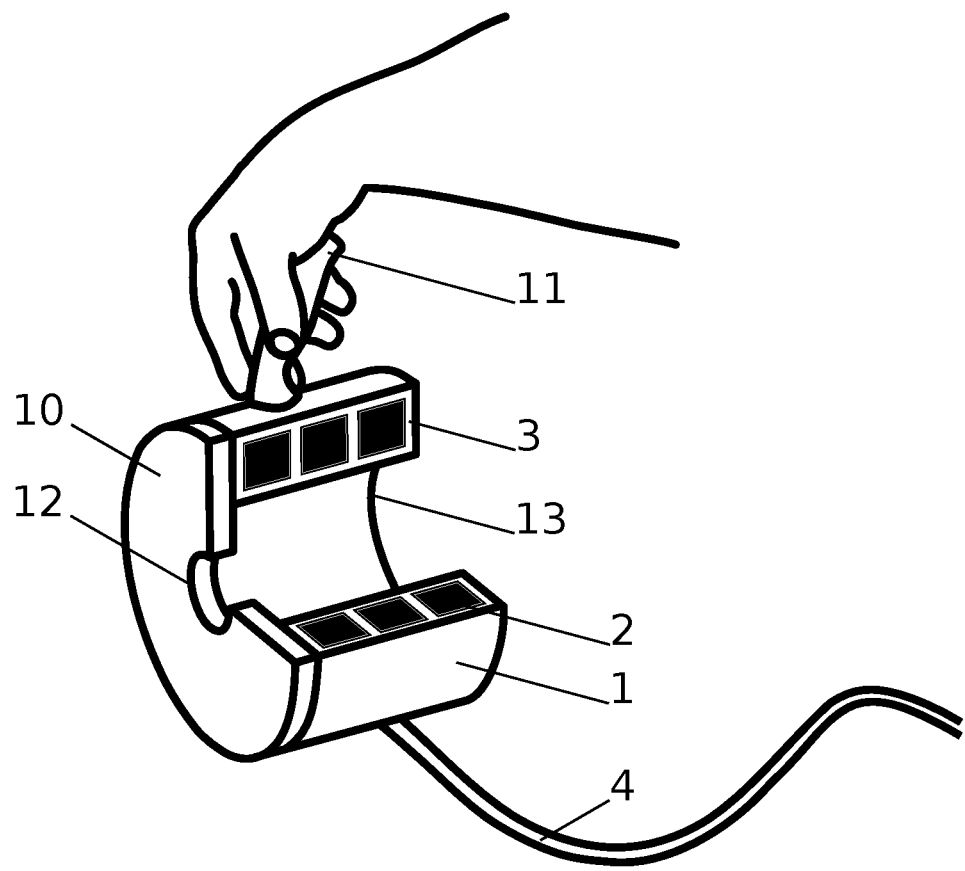
FIG. 7 shows a complex core with an electric field shaping element that is held by a hand by the means of a handle, in an offset section.

In the embodiment shown in FIG. 7 the complex core 1 with an electric field shaping element 10, which is made from an electrically non-conductive material, is tightly connected to the encasement 3 by the means of clip fasteners, allowing for shaping of the lines of the electric field generated by the system. The component cores 2 are separate toroids that encircle the opening of the encasement 3. A handle 11, which allows for a convenient hold of the device by a hand, is located in the preferred embodiment in a location, where the value of the electric field is sufficiently low, so that it does not considerably affect the hand.

Figure 8:
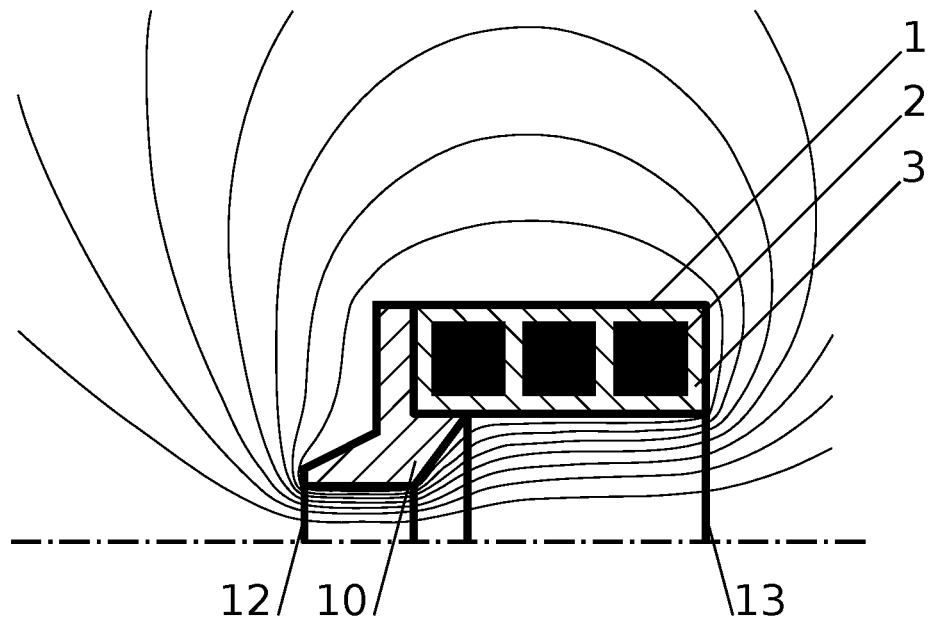
FIG. 8 shows a complex core with a separable electric field shaping element, which is immersed in a conducting medium, with visible electric field lines, in a half-section.

In the embodiment shown in FIG. 8 the complex core 1 was shown with the separably mounted electric field shaping element 10, which creates a tight press fit with the encasement 3, allowing for a local increase of the density of the electric field lines which are depicted in the figure. The torus-shaped component cores 2 encircle the opening of the torus-shaped encasement 3. Due to the fact, that the electric field shaping element 10 is made from electrically non-conductive materials, it shapes the flow of the induced current so that it flows approximately tangentially to its surface. The thin lines in the figure depict the electric field lines after the shaping of the current flow is established. The density of the electric current that enters the system through an opening near the medium 13 increases inside the electric field shaping element 10, becoming significantly greater in the vicinity of an opening near the body 12. In this case, the opening near the medium 13 is also the inner opening of the complex core.

Figure 9:
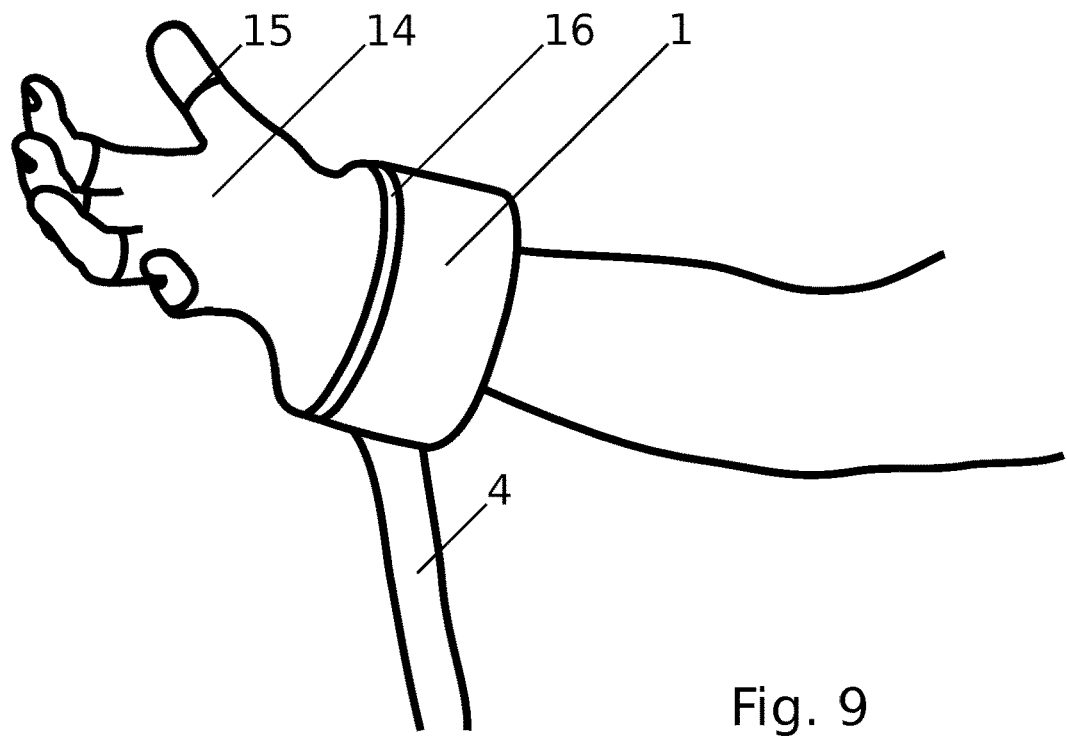
FIG. 9 shows a complex core with an electrically non-conductive membrane, which is put on a hand.

In the embodiment shown in FIG. 9 an electrically non-conductive, elastic membrane 14 is put on a hand, allowing for a local increase of the electric current density in the areas where membrane openings 15 are situated. The inside of the membrane 14 is hollow, which in this case allows to put it on the object that is affected and provides continuity of the current induced by the complex core 1, which flows inside the membrane 14 approximately tangentially to its surface and flows outside through the membrane openings 15. A membrane connector 16 provides a tight connection between the membrane 14 and the complex core 1, allowing as well for attaching and detaching membranes of various shapes.

Figure 10:
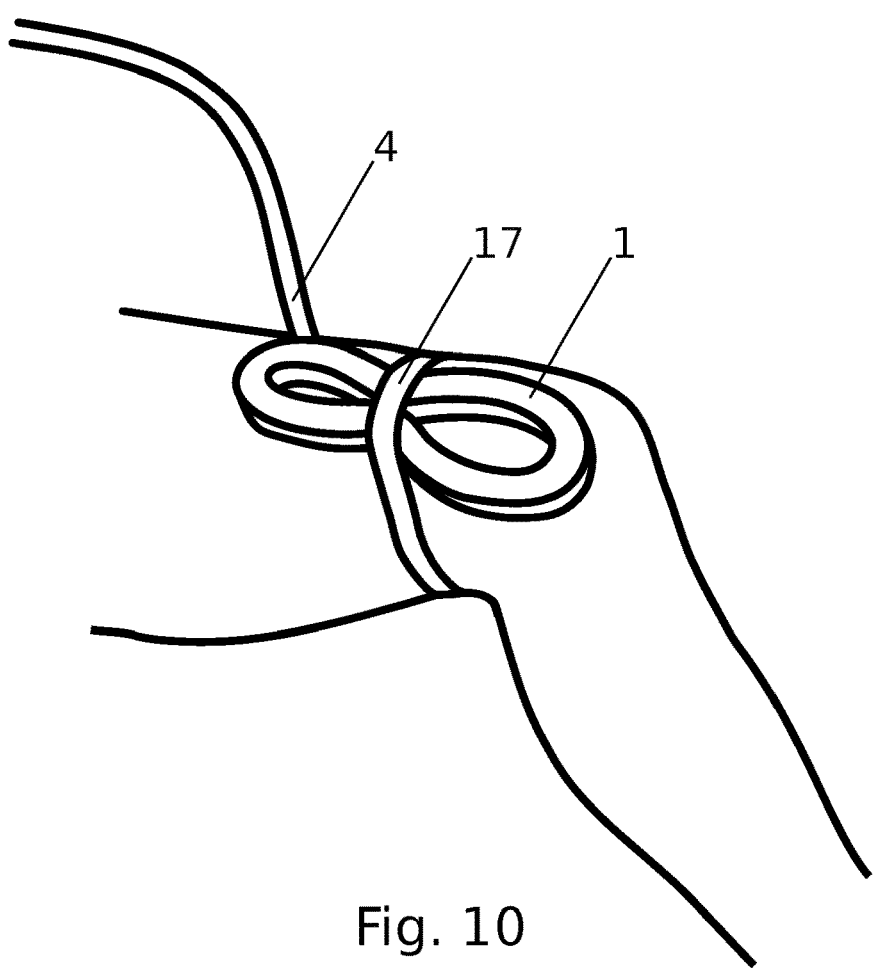
FIG. 10 shows an elastic complex core that is retained on a leg by the means of a band. In all the drawings a complex core is placed inside a conducting medium. The invention is also explained in an exemplary embodiment presented in figures, where

In the embodiment shown in FIG. 10 the elastic complex core 1 was laid on the surface of a thigh in order to affect the innervation of the knee. The ability to change the shape of the elastic complex core 1 with ease allows for an arbitrary shaping of the area that is affected by the electric field. An adjustable band 17 allows to conveniently fix the location of the affected area.

Figure 11:
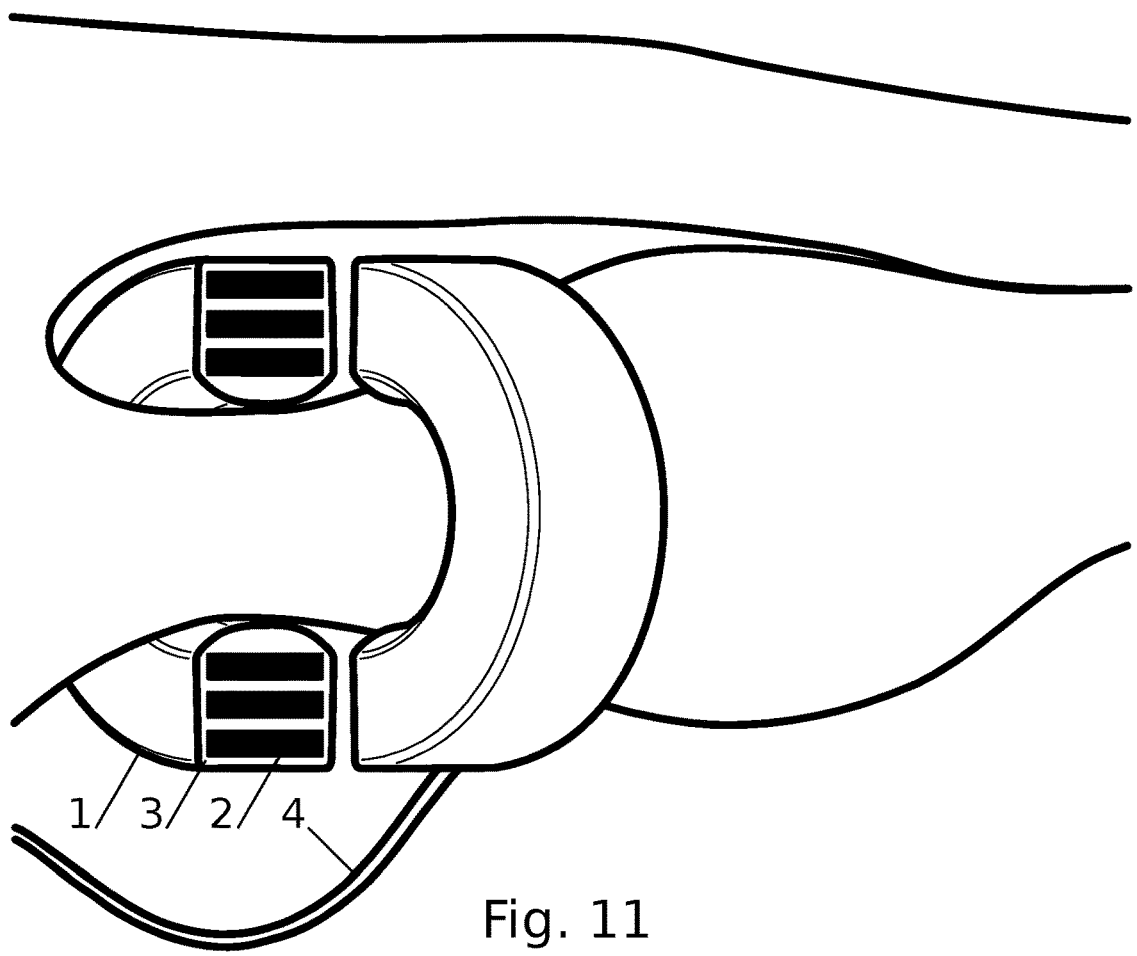
FIG. 11 shows two parts, that form a complex core after they are joined together, which are put on the dorsal root of spinal nerve.

The FIG. 11 shows two parts, that form the complex core 1 after they are joined together. Each of said parts comprises two surfaces of the interconnection which are configured to be joined with matching surfaces of the interconnection of the other part. The surfaces of the interconnection are located on both sides of each part, wherein each surface of the interconnection is a flat surface formed by the cross-section of the component cores 2 and the interior of the encasement 3 that is made from a solid material, which are flat and coplanar. The surfaces of the interconnection are perfectly matched to each other so that the joining of the parts results from the process of wringing, as in the case of Johansson gauges, which provides excellent magnetic properties of the complex core created in this way. As shown in the figure, the complex core in the form of an implant may be put on the dorsal root of spinal nerve without cutting the dura mater. This allows for a selective block of the sensory nerves that eliminates the feeling of the pain without affecting the ability to move. Due to the fact, that the complex core 1 induces flow of the current through a nerve without using any electrically conductive elements in contact with the body, the system according to the invention is insensitive to fibrous tissue growth, which occurs often after the implantation.

Figure 12:
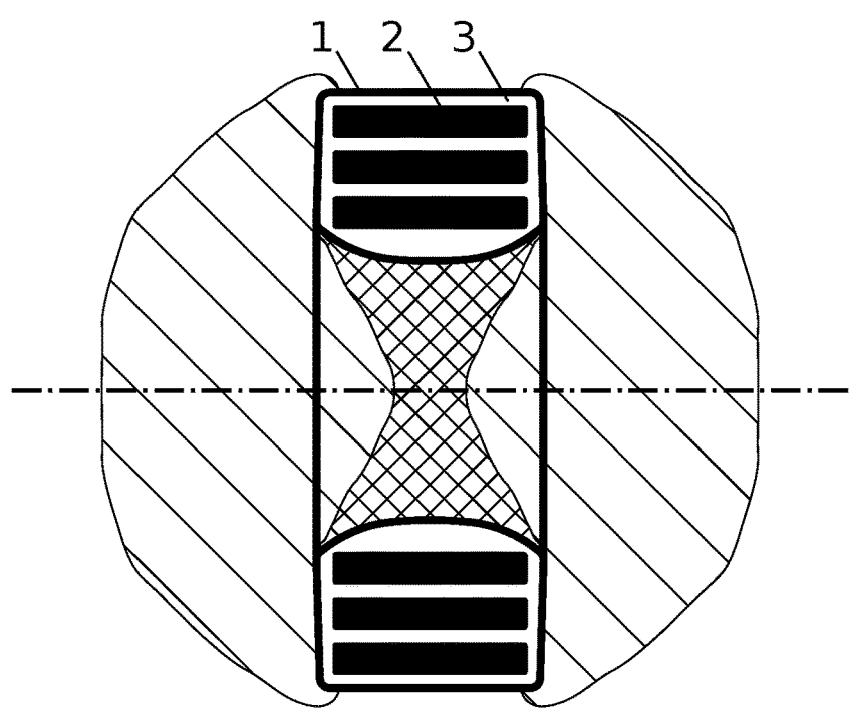
FIG. 12 represents the density of the current generated by the complex core from FIG. 11 after the parts are joined with two hatchings, with one of the parts of the complex core visible.

The FIG. 12 shows the density of the induced current inside the conducting medium 7 after joining of the parts of the complex core 1 from FIG. 11. The cross-hatched region corresponds to the area where the magnitude of the induced current density is homogeneous and ranges from 75% to 100% of the maximum density of the induced current. Due to the fact, that the complex core creates the area with a high degree of homogeneity of current, it is possible to uniformly affect all of the nerve fibers of the dorsal root of spinal nerve. The area outside the cross-hatched region and the diagonally hatched region corresponds to the area where the magnitude of the induced current density is smaller than 10% of the maximum density of the induced current. For this reason, the strength of the affection is insignificant in this area, also due to the small gradient of the current density. Due to this property, it is possible to selectively affect the dorsal root of spinal nerve and the dorsal root ganglion without affecting the ventral root of spinal nerve.

Figure 13:
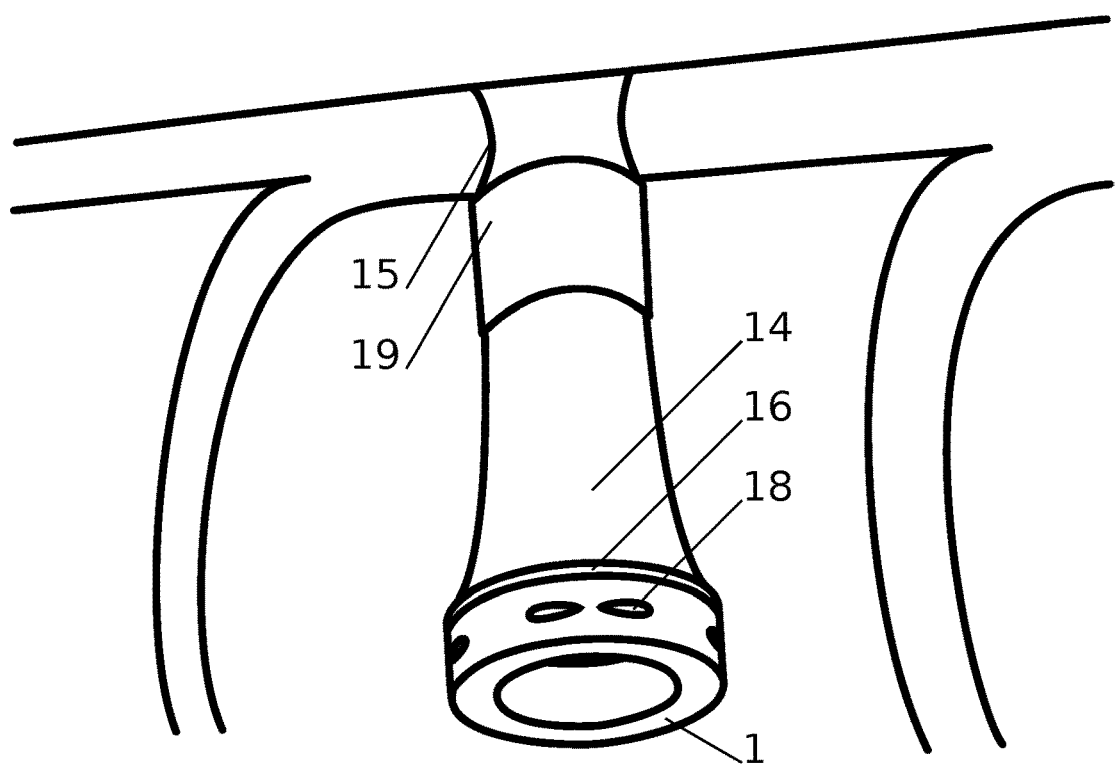
FIG. 13 shows a complex core inside the body, with a membrane that surrounds one of the nerve branches.

In the embodiment shown in FIG. 13 the complex core 1 that is placed inside the body selectively affects branches of a nerve by the means of the induced current flowing inside the membrane 14, which is joined to the core by the membrane connector 16. A portion of the membrane 14 is wrapped around the nerve and sealed by a sealing band 19, thus creating the membrane openings 15, through which the induced current flows. The complex core may be fixed in place by the means of through hole fixing openings 18, that allow for threading of surgical sutures in order to sew the complex core to durable tissues.

Figure 14:
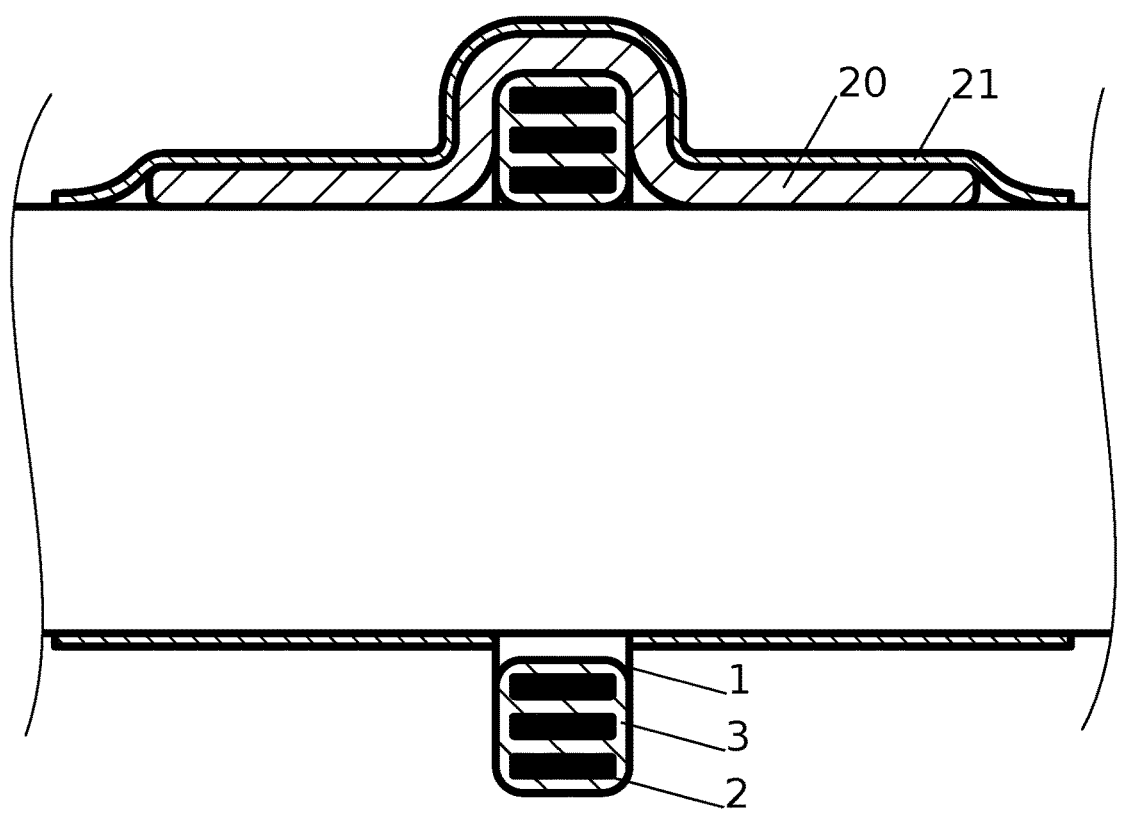
FIG. 14 shows a complex core put on a limb, with a gel slab that provides the continuity of the current flow, in a half-section.

In the FIG. 14 the complex core 1 is put on a limb and a gel slab 20 provides the continuity of the induced current flow. The component cores 2 are separate toroids. The gel slab 20 is made from an electrically conductive gel in the form of a solid body that retains its shape, characterized by an ability of reversible bending. The gel slab 20 is matched in shape to the complex core 1, which increases its durability. The whole ensemble is fixed to the limb by the means of an elastic fixing band 21, which enables to wear the device on the body, allowing for a mobile therapy.

An important challenge associated with systems for inducing an electric field in a conducting medium by the means of cores is to ensure that as much as possible of the induced current goes inside the body or into the object that is affected. Cores that are known from the prior art have some pre-determined shape, therefore an attempt to affect objects, which may have shapes that are complex or change with time, causes losses resulting from the flow of the current through this part of the inner opening of the core that is not occupied by the object that is affected, hereinafter referred to as the clearance. In view of the fact that all of the current induced by the core enters trough its inner opening, a portion of the object which is affected that is located in the inner opening and the clearance may be approximately treated as resistors connected in parallel. The losses are especially large when the total resistance of the clearance is low, since then the current flows mainly through the clearance bypassing the object that is affected. The system for inducing an electric field according to the invention solves this problem by providing a tight contact between the core and the object that is affected by the means of the electrically non-conductive encasement that encompasses the core, which is made from a material that is capable of a reversible change of shape by a small force, thus eliminating the losses caused by the flow of the current through the clearance. This does not exclude a design, wherein the encasement 3 may be made entirely from electrically non-conductive, stiff materials, such as ceramics or plastics, so that the encasement shapes the flow of the current inside the conducting medium without providing a sealing that would decrease the losses caused by the flow of the induced current through the clearance. In the preferred variant the encasement 3 encompasses at least two component cores 2 creating a complex core 1, which allows for the increase of the electromotive force generated by the system, that is powered with a low voltage. This does not exclude a design, wherein the encasement encompasses a single core.

The encasement should be made from an electrically non-conductive material in order to avoid chemical reactions that would occur on its surface if the current flowed through it. An appropriate shape of the encasement enables to shape the flow of the current in enclosed loops around the core in an arbitrary way. The reason for this is that the current induced in the conducting medium may not flow through the electrically non-conductive encasement and therefore flows in a direction that is approximately tangential to its outer surface. A part of the encasement 3 that constitutes a filling of the complex core 1 may be produced from stiff materials, provided that a portion, or, in the preferred embodiment, all of the outer surface of the encasement is made from a material capable of a reversible change of the shape by a small force, such as a silicone, a rubber, a plastomer or elastomer foam or a mixture of these materials. In particular, the outer surface of the encasement 3 may be made from a stiff, electrically non-conductive material with the limp seals 9 situated on this surface in some places. Preferably, the interior of the encasement 3 surrounds the component cores 2 to fix them in place. In the preferred embodiment the interior of the encasement 3 is made from an electrically non-conductive material, such as a plastic, a ceramic or a material that is suitable for its outer surface, in order to avoid losses associated with an unwanted flow of induced current around the component cores 2. In an exemplary method of production the encasement 3 is created by pouring the component cores 2 with a material such as a silicone, which takes the form of a flexible solid body after curing. An important advantage of the elastic encasement is that it provides greater comfort for the patient by lowering the risk of damages and enabling to rest comfortably on the core. The encasement also prevents movement between the cores and allows for easy positioning of the complex core on patient's body. It is also important that it protects the component cores from corrosion and mechanical damages.

In one of the variants the encasement 3 may be elastic enough in order to provide a tight contact with the body by a small force, thus limiting the losses resulting from the flow of the current between the core and the body, which lower the current that directly affects the nerve fibers. In the preferred embodiment the shape of the encasement may be changed with ease by strength of hands. When all of the outer surface of the encasement is elastic, a sealing that lowers the losses of the current may be obtained in case of the core that is put on the body, as well as in case of the core that is put near the surface of the body. In the preferred embodiment the hardness of the encasement is lower than 80 OO, in a more preferred embodiment lower than 50 OO and in the most preferred embodiment lower than 20 OO in Shore scale OO. The thickness of the encasement should be chosen in such a way that it could fill unevennesses of the object that is affected, thus creating a tight contact. In the preferred variant the thickness of the elastic, outer surface of the encasement is greater than 1 mm, in a more preferred embodiment greater than 3 mm and in the most preferred embodiment greater than 10 mm. In case of the complex core intended for implantation and affecting nerves of a small diameter the outer surface of the encasement may have a thickness of about 0.3 mm or smaller. The use of the encasement having a large thickness and high elasticity allows for sealing of the objects of significantly different shapes. An exemplary application of this variant of the invention is to provide a tight contact between the encasement and a forearm or a thigh. In this case, the complex core 1 should be pulled up so high, that the deformation of the encasement creates a full sealing with the contact surface. In some variants the encasement may be used only as a partial sealing, for example only for the inner side of the forearm, which enables to control the place where the nerve fibers are affected. In order to further increase the elasticity of the encasement one may use methods known from the state of the art, such as placing chambers filled with gas inside the encasement, which serve as a material recess. In some variants the outer surface of the encasement 3 is furnished with thin-walled chambers filled with a gas under pressure, which resemble a balloon in their shape. The use of such chambers enables to obtain a sealing by a small force between the encasement and the object that is affected by the electric field.

In order to provide a sealing for objects of significantly different dimensions, as well as to decrease the force required to obtain a tight contact, it is preferred to use the seal 9, which may be made in different variants, for example in FIG. 1 and FIG. 5b as a lip seal, and as densely packed, limp rods made from an elastomer as shown in FIG. 5a. The seal 9 may be made in different places on the outer surface of the encasement 3, for example inside the opening or on the side walls of the complex core 1 so that a tight contact is facilitated also in the positioning shown in FIG. 10.

The shape of the seal 9 should be chosen so that it is capable of reversible bending by a small force, for example by strength of hands, enabling to obtain a tight contact with the skin, thus allowing the use of the same complex core 1 for various parts of the body. Reversible bending means that the seal 9 is capable of returning to the original position after the force ceases to act, in some variants it may bend like a spring. The use of the seal 9 also enables to provide a tight contact with an object whose shape changes with time, for example for human chest during breathing. The ability to bend significantly by a small force may be obtained with methods known from the state of the art, by at least local forming of the seal 9 so that it has a low second moment of area. The cross-section of the seal 9 may be also substantially smaller than its length. Such a shape allows for making the seal 9 from elastomers, plastomers and other materials that are electrically non-conductive, which become sufficiently limp when suitably formed. Therefore, the seal 9 may be made from a different material than the encasement 3, for example the encasement may be made from a silicone and the seal from a plastic film. In the preferred embodiment the seals 9 and the encasement are merged, although this does not exclude a design, wherein a change of the seals is possible by the means of a suitable connector, which is separably connected to the encasement. In some variants the seals 9 are situated on the outer side of a coat made from an elastomer, whose inner surface matches the outer surface of the encasement 3, thus enabling to attach and detach the coat to the encasement many times, which allows for changing of the seal 9. In some variants, in order to provide a better contact, the seal 9 may be pressed against the surface of the object that is affected by the means of the methods which are known from the state of the art, for example, by tightening with an adjustable belt or an elastic band.

Due to the fact that the current flowing through the inner opening of the core may only bypass the seal 9 and flow inside the opening through the conducting medium 7, it is preferable to use a larger number of seals 9 inside the opening of the complex core 1. In one of the variants the seals 9 may take form of densely packed, thin rods made from an elastomer or plastomer that resemble hair as shown in FIG. 5a. It is also possible to utilize seals 9 having an arbitrary shape, provided that they are densely packed and are sufficiently limp, for example one may use strips or flaps made from a plastic film of an arbitrary shape. Due to their high limpness, the seals 9 in the form of the hair provide a tight contact with the encasement 3 for objects of any shape, whereby after the object is put through the opening of the complex core, or the complex core is put near the object that is affected, the hair create a barrier between the object and the encasement 3, which significantly increases the resistance of the clearance. The use of different variants of the seals 9 is particularly beneficial in case of the encasement 3 made from a stiff material.

Due to the fact that the current flows around the encasement and other electrically non-conductive elements it is possible to shape the flow of the current, for example in order to increase the current density in a chosen location. This may be achieved by an inner opening of the encasement having a resizable diameter or by forming the encasement so that it takes a shape that was obtained through an optimization which was carried out utilizing computer simulations of the electric field lines. Although in order to shape the current flow one may use the encasement 3 that was suitably formed beforehand, in the preferred embodiment one may obtain a change of the electric field lines pattern by replacing the electrically non-conductive electric field shaping element 10, that may be detached and tightly attached to the encasement 3 by the means of clip fasteners, a direct or indirect press fit, or by the means of other methods that provide a tight, separable connection, which are known from the state of the art. The electric field shaping element 10 may take form of a plate or a solid and may comprise openings, wherein, in the preferred variant, it is made from a material capable of a reversible change of shape by a small force, although this does not exclude a design, wherein a stiff material is used. For example, the electric field shaping element 10 may be made from plastics, ceramics or silicones. In case of use of the electric field shaping element 10 made from elastic materials it is possible to partially change the electric field lines shape by a suitable forming of this element also during the therapy. Due to the fact that electric field shaping elements 10 may have various shapes and may comprise arbitrarily placed openings, it makes it possible to change the shape of the electric field lines many times utilizing the same complex core 1. It is also possible to connect more than one electric field shaping element to a single complex core.

The FIG. 7 and FIG. 8 show an exemplary embodiment of the electric field shaping element 10 that is connected tightly to the encasement 3 so that the diameter of the opening near the medium 13 is larger than the diameter of the opening near the body 12, and the continuous conducting medium 7 is situated between the openings. Such a shape enables to increase the density of the current in the vicinity of the smaller opening, where the gradient and the intensity of electric field may be larger by an order of magnitude compared to a system having an opening of a constant diameter. In the vicinity of the opening near the body 12 a limited area that enables to strongly affect by the means of the electric field is created, allowing to locally affect the nerve fibers that are surrounded by a bone tissue or a thick layer of an adipose tissue, which are usually hard to reach. The area of increased intensity and gradient of the electric field may be shaped by a suitable design of the encasement, so that the gradient decreases significantly at a distance of a few centimeters from the opening, allowing for a precise determination of the range of the affection. The use of the electric field shaping element 10 in the form of a conical nozzle as shown in the FIG. 8 allows for obtaining a sealing between the nozzle and the body more easily due to reduction of the area of contact. The shape of the nozzle also enables to compress the skin in the place of affection, which allows to increase the range of affection of the device inside the body. In one of the variants the encasement 3 may be connected permanently or may allow for attaching and detaching of the handle 11 that facilitates the positioning of the complex core during the therapy as shown in FIG. 7. In the preferred embodiment the handle 11 is formed and placed in such a way that the intensity and the gradient of the electric field do not considerably affect the hand.

In the preferred embodiment the encasement encompasses each of the component cores completely and settles their position relative to each other, which allows for a tight packaging of the complex core. In this way the loops of current may have a small circumference, which enables to obtain a larger current compared to the case of loosely packed component cores. This does not exclude a design, wherein the encasement is a tight coat that encompasses the component cores and does not limit the movement of the cores inside it. It is also possible to make clip fasteners outside the encasement or utilize other known methods that allow to connect into a tight, structural whole the complex cores or single cores encompassed by the encasement, so that a joined encasement that was created in such a way encompasses all of the cores inside it and shapes the flow of the electric field. It is preferable to use methods that provide tightness of the join and distance between the cores that is as short as possible. The thickness of the encasement should be generally chosen so that it is as small as possible, provided that other requirements are satisfied, such as the ability to conform to the shape of the object that is affected. The use of the encasement having too large dimensions increases the circumference of the loop of the current that flows around it, thus decreasing the intensity of the current.

Due to the fact that the phenomenon of magnetostriction may cause vibrations of the core that are audible to humans, the encasement has preferably a suitable thickness, material properties and value of the acoustic impedance, chosen in in order to attenuate the acoustic waves generated by the core.

In the preferred embodiment the encasement is made from a material having a density that is smaller than the density of the surrounding conducting medium, which reduces the apparent weight of the core. In some variants the dimensions of the encasement may be chosen in such a way, that the weight of the complex core in the conducting medium is partially or completely balanced by the force of buoyancy, which facilitates the use of the system by patients. In order to achieve this goal the encasements may be furnished with chambers containing a gas or another material whose density is significantly smaller than the density of the conducting medium.

The encasement may also create or allow for attaching and detaching in any location an elastic, thin-walled membrane made from an electrically non-conductive material. This membrane allows to obtain a sealing and shape the flow of the current in various locations of the body, it may also have a shape that facilitates sealing of parts of the body that have a complex structure. For example, the membrane 14 may take shape of a glove or a sock with openings 15 in those locations that should be affected by the electric field as shown in FIG. 9. The Openings 15 in this variant may be also placed on the surface of a hand or in any other location on the membrane 14, whereby it is essential to provide a proper sealing at least in the vicinity of the each opening. The number, shape and location of the openings on the surface of the membrane 14 are completely arbitrary, although the use of a smaller number of openings having a small surface area allows to obtain a larger intensity and gradient of the electric field. The membrane 14 may enable to affect objects of arbitrary shape by the electric field also when the complex core may not be put on them, for example the complex core could be situated outside the arm, while the membrane 14 in the form of a sleeve could encompass the hand. In some embodiments the membrane 14 may be made from non-elastic materials, which provide a tight match to the object that is affected due to their limpness. The membrane may be made from electrically non-conductive materials, that allow for an easy change of its shape, such as a plastic film, a rubber or a silicone. In the preferred embodiment the thickness of the membrane is lower than 3 mm, in a more preferred embodiment lower than 1 mm and in the most preferred embodiment lower than 0.1 mm. In the preferred embodiment the membrane 14 is merged with a connector 16 that is joined with the encasement 3 by a press fit or by the means of clip fasteners, however, it is possible to use any method providing a tight, separable connection that is known from the state of the art. The membrane 14 may be also put directly on a sealing rim made on the edge of the encasement 3. In the preferred variant the membrane 14 is made from elastomers, although this does not exclude an embodiment, wherein it is made from different materials, such as plastomers in the form of a film. In some variants a tight contact between the membrane 14 and the body may be obtained by the means of a compression with the clamp 8. The possibility of connecting to the complex core 1 the electric field shaping element 10, that may change the strength of affection by the electric field on the surface of the body, and the membrane 14, which enables to shape the electric field after putting it on the body significantly increases the application area of the system according to the invention.

The electrically non-conductive elements, such as the encasement 3, the seal 9, the electric field shaping element 10 and the membrane 14 shape the flow of the current in the conducting medium. Although initially the current induced by the component cores 2 may be partially perpendicular to the surfaces of these elements, which are in contact with the conducting medium, due to the flow of the current some electric charges are quickly embedded on these surfaces, which stops embedding of the charges and directs the flow of the current approximately tangentially to said surfaces. In the preferred embodiment the time that is required for shaping of the flow of the induced current is lower than 1 μs, in a more preferred embodiment lower than 100 ns and in the most preferred embodiment lower than 10 ns. This time is determined by the conductivity of the conducting medium and the shape of the electrically non-conductive elements as well as their electric permittivity. It is preferable to utilize electrically non-conductive elements of sufficiently high thickness, which are made from a material having a low value of the electric permittivity, due to the fact that their capacitance is low in this case, therefore only a small electric charge embedded on their surface is sufficient to shape the flow of the current.

Due to the fact that the induced current flows around the encasement and other electrically non-conductive elements of the system, in the areas where the radius of curvature of these elements is small there may be a significant local increase in the density and gradient of the induced current, which locally increases the strength of affection. This phenomenon may be used in order to achieve a small and well defined area of affection on the nerves. In many applications, however, it is important to achieve homogeneous affection on all of the nerve fibers, for example in order to block the pain when affecting a nerve inside the body as in FIG. 11. In this case it is preferable to use the encasement and the electrically non-conductive elements of the system having the radius of curvature that is as large as possible. This goal may be achieved maintaining the encasement of a small size, for example by the means of the encasement having a variable radius of curvature along its surface, so that the portions having a smaller radius of curvature are located so far from the nerve that they do not affect it in a significant way. It is also preferable to use seals 9 having a radius of curvature that is as large as possible, as shown in FIG. 1 and FIG. 5b. It is particularly advantageous to use a shape of the surface of the encasement which has a variable radius of curvature, that was obtained through an optimization carried out utilizing computer simulations of the electric field, so that the induced current is homogeneous over a large area. An example of such a shape is shown in FIG. 12, wherein the area where the homogeneity of the current density is larger than 75% may cover the whole nerve as well as the surface of the encasement inside the opening of the complex core.

In some variants the system according to the invention uses magnetic cores characterized by an ability of a reversible change of shape by a small force, so that they may be shaped by the user with ease by strength of hands. In some embodiments the elastic core may be a unitary core that is optionally covered with an electrically non-conductive elastic encasement. Elastic cores may be also used as the component cores 2 which create an elastic complex core 1 after covering with an elastic, electrically non-conductive encasement 3. For this reason, whenever the text refers to a complex core it should be borne in mind that it may be in particular an elastic complex core. In the embodiment shown in FIG. 3a and FIG. 3b the complex core 1 was made completely from elastic materials, which allows for an arbitrary change of its shape in order to adjust the area that is affected by the electric field. Due to the fact that the intensity and gradient of the electric field have the highest value close to the surface of the core, the possibility to adjust the shape of the elastic core to the patient's limb enables to obtain a smaller distance to the nerve fibers and a stronger affection. The elasticity of the complex core also facilitates obtaining a tight contact with the body, thus eliminating the losses of the current through the clearance. This allows to use the encasement 3 having smaller elasticity or the seals 9 having smaller dimensions. The possibility of adjusting the shape of the elastic core to the object that is affected also enables to obtain a higher current intensity, due to shortening of the current loop length. When the complex core 1 is put near the surface of the body as in FIG. 10 the possibility to change the shape allows for a precise control of the area of the body that is affected by the core. It is also possible to reduce the area of the affection by a close placement of the portions of the loop of the complex core 1 as in FIG. 4 in such a way that the induced electric field is locally mutually canceled.

The elastic core may be made in various variants, that vary with the degree of elasticity. In the preferred embodiment the elastic core is pliable and under the action of a force it assumes a new shape that is retained until it is bend again. This does not exclude a use of the elastic core akin to a spring, that returns to the original position after bending, wherein in order to obtain the desired shape it is required to use a suitable fixing, for example in the form of the clamp 8 that fixes the shape of the core as in FIG. 4. The clamp 8 may be for example an elastic ring, an adjustable belt or a buckle.

In one of the variants the elastic core is made from a ferromagnetic tape, which in the preferred embodiment has a thickness from 10 to 100 μm. In order to reduce the losses caused by eddy currents and to increase elasticity it is preferable to use the tape having a thickness that is as small as possible. In the preferred variant the elastic cores are made from a tape made from alloys based on iron or cobalt, that is known by the name of amorphous or nanocrystalline tape, which in the preferred variant has a thickness from 15 to 30 μm. In order to retain the elasticity of the tape it is necessary to change the process of the heat treatment so that the tape does not become brittle, as is the case for the classic heat treatment after the core is wound. To achieve this goal one should determine experimentally the highest permissible temperature of annealing inside the furnace, as an alternative one may perform an additional heat treatment of the tape that was annealed in a classic way by a slow heating and cooling of the tape, in a similar way to the classic steel tempering, in order to decrease its brittleness. From the experience of the author the nanocrystalline and amorphous tapes are suitable for a direct use as a core without heat treatment, thus preserving their full elasticity, and their magnetic properties may match that of the ferrite cores. The provided examples of embodiments of the elastic core depend on alloys based on iron or cobalt, although this does not exclude the use of different materials having good magnetic properties, which are characterized by a sufficient elasticity at a certain thickness, as well as the use of magnetic fluids.

Although the elastic core made from a nanocrystalline tape may be utilized directly in the system, in order to decrease the losses resulting from eddy currents it is preferred to cover the tape with a thin layer of an insulator. Preferably, the insulator has a small thickness so that it does not change considerably the fill factor of the core and does not substantially influence its elasticity. According to the art, to achieve this goal one may use a coating of a magnesium oxide or a lacquer. If the heat treatment of the core does not require high temperatures it is possible to use the insulator in the form of a thin layer of an elastomer, such as the PDMS, or to cover the tape with a layer of a grease or an oil. In the preferred method of production the tape is continuously covered with a thin layer of an insulator on one side during the winding of the core.

The use of a low supply voltage to improve patient safety results in a significant decrease of the electric field intensity that is induced by a single core in the system known from the state of the art. The electromotive force, abbreviated emf, which is generated by the core in the conducting medium is approximately equal to the supply voltage divided by the number of the winding turns, it is therefore advantageous to make the number of the winding turns as low as possible and in the preferred embodiment it is a single turn winding. In spite of the small number of the winding turns the emf of the system may still be insufficient to achieve the desirable affection on the nervous system. For this reason it is preferable to use a larger number of arbitrarily placed cores, each of them connected in parallel with the power-control system in such a way that the emf generated by the individual cores adds together, totaling to an electric field intensity and gradient that is sufficient to obtain the desirable affection on the nervous system. In the system according to the invention the component cores 2 are encompassed by the electrically non-conductive encasement 3, creating the complex core 1 as shown in FIG. 2a. The use of the encasement eliminates losses resulting form the tendency of the current to choose the path of the lowest resistance around the component cores, which decreases the total current affecting the patient.

The cores may have various shapes and cross sections. In the preferred embodiment of the system the maximum value of the magnetic flux density of each component core changes in the same way in time so that all of the component cores reach saturation magnetization at the same time. This does not exclude an embodiment, wherein individual component cores have different values of magnetic flux density in time. Individual cores may be made from materials having different magnetic properties. In some embodiments the electric currents flowing through the windings of the component cores may be distinguished by different time courses. In one embodiment some of the cores possess windings that have more than one turn, or one core is wound with several windings connected in parallel, which allows to use wires having a smaller cross section. It is particularly advantageous to place the component cores 2 along the radius of the complex core 1, as in FIG. 5b, due to the fact that this allows to significantly reduce the effect of the decrease of the magnetic flux density along the radius. For this reason it is possible to obtain the desirable emf of the complex core with the use of the cores having smaller dimensions and weight, which improves the ergonomics of the device. In some embodiments the component cores are placed in a different, arbitrarily chosen way, for example by the placement of the component cores 2 of arbitrary shape along the radius and the axis of the complex core 1, as shown in FIG. 2a. In the preferred embodiment the component cores 2 have matching shapes and are placed close to each other, which allows for smaller circumference of the current loop resulting in a higher induced current.

In order to allow for the independent change of magnetization of each of the component cores 2, the number of the windings 5 should be equal to or larger than the number of the component cores. Therefore, in the preferred embodiment each component core is wound with a separate winding. In some cases the component cores may change their magnetization independently to reach saturation magnetization at substantially the same time if the windings are wound around them in a more elaborate way. For example, in case of three component cores A, B and C, wherein first winding is wound around the cores A and B, second winding is wound around the cores B and C, and third winding is wound around the cores C and A, the independent change of magnetization of each component core may be achieved by an appropriate control of the changing currents flowing through the windings. Similar designs may be utilized for any number of cores, wherein in some cases at least one winding may be wound around each unique combination of the component cores.

The subject of the invention is also a method for designing the complex cores, wherein from each unitary core powered with a high voltage one may extract in thought a set of smaller, closed component cores which are placed close to their original position and are powered by parallel windings in such a way, that the emf of the complex core which is close to the original emf is generated by the means of a significantly smaller voltage. The cores or windings are connected in parallel when the voltage difference between the ends of the wires 6 that supply the current to the given winding 5 is equal for each of the windings. In order to achieve this goal, in some embodiments the ends of the wires 6 that power different component cores may be connected. Due to the division the current that flows through the system increases proportionally to the voltage reduction, although due to distribution of the current between the wires connected in parallel this does not create a significant increase of conduction losses. The division of the core in the design stage may be achieved in various ways, depending mainly on the ease of production and the ability to efficiently place the wires 6 and the windings 5. In a particularly advantageous embodiment the wires 6 leave the complex core close to each other so that it is possible to put them together into a single cable 4 that leads to the power-control system. The cable 4 may be completely filled with an insulating material or may comprise a coat that screens the wires 6. An essential feature of the system according to the invention, which allows for the arbitrary packaging, is the insignificant interaction between the individual cores due to confinement of the magnetic field lines inside them, as opposed to the air core coils, where the influence of mutual inductance is considerable.

An important advantage of the system according to the invention is the effective use of the material properties of the magnetic cores by an increase of the magnetization homogeneity of each of the component cores. As an example, consider the complex core 1 comprising several component cores 2 placed along the radius, as shown in FIG. 5b. Ampere's law dictates that the value of the magnetic flux density B inside the core changes along the radius r according to the equation $$B = \frac{\mu I}{2\pi r},$$

where $\mu$ is the magnetic permeability of the core, and I is the total current flowing through the winding. After integrating this equation over the radius one obtains formula for the inductance $$L = \frac{\mu N^2 H}{2\pi} \ln\frac{b}{a}$$

where b and a are, respectively, the outer and inner core radius, H is its thickness, and N denotes the number of the winding turns. Assuming that the cores are powered in parallel with the same voltage U, the windings have similar resistance R and the rise time of the current is short compared to the time constant $$\tau = \frac{L}{R}$$

the formula $$U = L\frac{dI}{dt}$$

predicts that the current intensity changes with time t approximately inversely proportionally to the inductance $$I(t) \approx \frac{U}{L}t.$$

By combining these expressions together we obtain the formula $$B(t) \approx \frac{Ut}{N^2 H \ r \ \ln\frac{b}{a}}.$$

Due to the fact that the highest value of the magnetic flux density occurs at the inner core radius, in an optimal embodiment at the end of the rise time it reaches the saturation magnetization or other experimentally determined value which allows for avoiding nonlinearity of the magnetization, therefore we strive to achieve $$N_1^2 H_1 a_1 \ln\frac{b_1}{a_1} = \ldots = N_i^2 H_i a_i \ln\frac{b_i}{a_i} = \ldots = N_n^2 H_n a_n \ln\frac{b_n}{a_n}$$

for each of the n component cores.

This goal may be reached in a variety of ways, by changing the number of the winding turns or the dimensions of the cores. To restrict our attention an efficient packing $b_i \approx a_{i+1}$ is assumed as well as N=1 and the same H for each of the cores. In case of two component cores we obtain an exemplary solution as shown in FIG. 5a with the dimensions $b_2=5$, $a_2=b_1=3.5$ and $a_1=1.618$ expressed in arbitrary units. For three component cores we obtain the system as shown in FIG. 5b with $b_3=5$, $a_3=b_2=4$, $a_2=b_1=2.958$ and $a_1=1.803$. In some embodiments, for example in case of a larger number of the component cores, the value of $b_i-a_i$ obtained as a result of the optimization remains approximately the same. In case of the component cores having more elaborate shapes, for example as shown in FIG. 2a, the requirement for the cores to reach the saturation magnetization at the same time may be fulfilled by the means of a numerical optimization with the use of computer simulations.

The FIG. 6 features a graph comparing change of the value of the magnetic flux density along the radius for the complex core from FIG. 5b, which is represented on the graph with a thick line, and for a single core having the same inner and outer radius, that is represented on the graph with a thin line. The value of magnetic flux density B shown on the vertical axis and distance from the axis of the core r depicted on the horizontal axis were expressed in arbitrary units. By analyzing the graph one may notice that the complex core enables to obtain a magnetic flux that is more than 45% higher compared to a single core having the same dimensions.

The use of the complex core enables to sum the emf generated by the component cores, although it is the shape of the encasement that determines the resultant density of the current. Due to the fact that the density of the current inside the opening of the complex core is significantly larger than the density of the current outside, the majority of the voltage drop occurs inside this opening. For this reason it can be concluded that for a toroidal complex core the current intensity inside its opening is roughly proportional to the emf divided by the length of the opening. In case of a complex core comprising n component cores which are placed along its radius without changing the length of the opening this means that the intensity of the current in the opening is increased approximately n times compared to a single component core. This arrangement is particularly advantageous due to an efficient increase of the intensity and gradient of the electric field, which enables to obtain a significant strength of affection. In case of the complex core comprising component cores which are placed along its axis the electric field intensity inside the opening of the complex core also increases with the number of the component cores, although less efficiently than in the case of the component cores placed along the radius if the length of the complex core needs to be increased. This arrangement, however, makes it possible to affect a larger area and enables to obtain better homogeneity of the current inside the opening.

It is particularly advantageous to use the system according to the invention in the form of implants affecting nerves inside the body. The use of the encasement 3 having a suitable shape enables to obtain a uniform strength of affection on all of the nerve fibers inside the nerve on which the core is put on. With the use of the seal 9 the induced current is efficiently directed inside the nerve, which significantly decreases the energy consumption of the device. Due to the fact that the area of the increased current density is homogeneous and well defined, as shown in FIG. 12, it is possible to affect a selected nerve without affecting adjacent nerves. For example, it is possible to affect the dorsal root of spinal nerve, which selectively blocks sensory nerves and the feeling of pain, without affecting the ventral root of spinal nerve, thus maintaining the ability to move the body, as shown in FIG. 11. The complex core as shown in FIG. 12 induces the flow of current which is also characterized by a high homogeneity of a component of the gradient of the current density that is parallel to the axis of the core, thus enabling to obtain a similar rise time of the membrane potential for the similar nerve fibers regardless of their position inside the nerve. Due to the lack of the electrically conductive elements in contact with the body fluids, the system according to the invention is also insensitive to a build-up of the scar-tissue, that often occurs after implantation.

Putting the core on a nerve during a surgery usually requires a use of at least two parts that may be joined together to form the complex core, as shown in FIG. 11. Each of said parts comprises surfaces of the interconnection which are configured to be joined with surfaces of the interconnection of other parts. The term surfaces of interconnection has the same meaning as surfaces of the interconnection. In the preferred embodiment the surfaces of the interconnection of the complete complex core are parallel to its axis, although this does not exclude an embodiment, wherein the surfaces of the interconnection have an arbitrary shape, provided that they match together. In order to achieve an efficient induction of the emf it is essential to ensure the shortest possible distance between the joined parts of the component cores, due to the small magnetic permeability of the air gap. This can be accomplished by providing a suitable surface finish to the surfaces of the interconnection with the methods known from the state of the art, for example by the means of lapping or polishing. It is also important to assure a constant contact force of sufficiently high magnitude between the surfaces of the interconnection.

In the most preferred variant the complex core is created as a result of joining of two parts having perfectly matched surfaces of the interconnection by wringing them together, as in the case of Johansson gauges. Joining in this way enables to obtain an air gap whose thickness is about 25 nm or lower, which provides excellent magnetic properties of the complex core. A manual check to see if the parts of the complex core are wrung together may be performer with ease during the surgery, which ensures that the complex core was joined with a sufficient precision. The surfaces of the interconnection may have an arbitrary shape, although flat surfaces characterized by a surface roughness Ra of 0.025 µm or better and a flatness of at least 0.125 µm are preferred. In some variants of the invention the finish of surfaces of the interconnection is not as good and does not allow for joining by wringing. In these variants as a result of pressing the surfaces of the interconnection together an air gap having a thickness smaller than 30 µm is created, in the preferred variant its thickness is smaller than 10 µm, and in the most preferred variant it is smaller than 1 µm. In order to check, if the assembled complex core meets the requirements the power-control system may also measure the inductance of the component cores utilizing methods known from the state of the art. It is preferable to use the component cores and the interior of the encasement which are made from stiff materials that are suitable for a precision machining, for example ceramic materials, in order to provide a precise match of the joined surfaces of the interconnection. The use of the component cores made from materials which do not meet these requirements, for example cores made from a nanocrystalline tape, is possible when the surfaces of the interconnection are covered with a stiff, well matched intermediary material having good magnetic properties, for example a ferrite, which is joined with the component cores. It should be emphasized that the component cores may be locally joined together by a material having good magnetic properties, and as long as the volume of the joining material remains low compared to the total volume of the component cores it is possible to obtain a good homogeneity of magnetization, for example one that is shown in FIG. 6 with a thick line. In the preferred variant the ratio of these volumes is lower than 5% and in a more preferred variant it is lower than 1%. In the most preferred variant the component cores are completely separated from each other. For this reason in some variants of the system according to the invention the whole of the surfaces of the interconnection may be made from a thin and uniform layer of ferrite, which is joined with each of the component cores at one side so that the magnetic permeability of this join is as high as possible. In some embodiments the surfaces of the interconnection may be made from various materials, wherein only a material that is adjacent to a component core should have good magnetic properties. It is also possible to utilize component cores having well matched surfaces of the interconnection that are placed inside the encasement made from an elastic material, that does not have to be characterized by well matched surfaces of the interconnection. In some embodiments the parts of the component cores have well matched surfaces of the interconnection that protrude beyond the surface of the cross-section of the interior of the encasement, which positions the cores relative to each other, so that the surfaces of the interconnection join the component cores, and the interior of the encasement does not have to be characterized by well matched surfaces.

Due to the fact that the seal and the outer surface of the encasement may have an ability of reversible change of shape by a small force, the outer surface of the complex core remains tight after its parts are joined together. In order to achieve a tight connection one may utilize methods known from the state of the art, for example the outer surface of the encasement may protrude beyond the surfaces of the interconnection in such a way, that after joining the parts together there is a compression as a result of the contact of the protruding portions of the encasement. In some variants this protruding part of the encasement may be rolled up like a sleeve, so that it does not interfere with the joining, and then straightened to its original position, in order to ensure the tightness of the outer surface of the complex core.

The described methods of manufacture enable to obtain a good match of the surfaces of the interconnection, although in order to provide a constant contact and a good match between the parts of the complex core it is preferable to use direct or indirect fastening methods and fasteners that are known from the state of the art. In some variants the parts of the complex core may be joined separably and positioned relative to each other with the use of a threaded connection, for example using at least one countersunk screw screwed into a threaded hole made in one of the parts, whose head rests on a conical hole made in the other part, thus creating a contact force between the parts of the complex core. It is also possible to utilize connectors screwed into the encasement, which join and position the parts of the complex core, as well as clip fasteners, magnets, clamps and other joining techniques that are known in the state of the art. In some variants the parts of the complex core may be joined and positioned relative to each other by the means of well matched protrusions and cavities made in the surfaces of the interconnection, which allow for a press fit.

The use of the seal allows to direct most or all of the induced current inside the nerve, which is particularly advantageous due to the electrically insulating layer of fatty tissue inside the epineurium that shields the nerve. In some embodiments the system according to the invention enables to maintain a constant contact of the sealed portion of the nerve with the body fluids in spite of the reduction of the current flow through the clearance. This goal may be reached by the means of the seal 9 having a shape similar to that of a helix, whose axis is collinear with the axis of the complex core, or by the means of a labyrinth seal, which maintain continuous flow of the body fluids despite much larger resistance of the clearance. A similar effect may be achieved by using the seal or the encasement made from a porous material or by the means of a seal in the form of densely packed, limp rods, as shown in FIG. 5a.

It is preferable to use the encasement and other electrically non-conductive elements of the system that provide a tight contact with a nerve utilizing the lowest possible pressure. This goal may be achieved by the means of the encasement that comprises numerous empty chambers so that the material of the encasement creates a loose elastic mesh. In one of the variants of the invention the encasement has at least one chamber, which may be filled with a liquid or a gas at a low pressure after the complex core is put on a nerve. In the preferred embodiment said pressure is lower than 300 mbar, in a more preferred embodiment lower than 100 mbar, in an even more preferred embodiment lower than 20 mbar and in the most preferred embodiment lower than 5 mbar. It is preferable to use biocompatible filing substances, for example a saline or an air. It is particularly advantageous to fill the chambers with air, which provides a small, stable pressure on a nerve in any position of the body and ensures insensitivity to potential changes in shape. It is also possible to utilize a combination of these methods, wherein the chambers inside the encasement may be filled during manufacturing or during the surgery with fluids having various physical properties.

Preferably the encasement has suitably chosen shapes and radii of curvature which enable to obtain a homogeneous flow of the current, for example one shown in FIG. 12. In order to provide a tight contact between the encasement and a nerve while maintaining the optimum shape of the outer surface of the encasement adjacent to the nerve one may utilize the encasement made from materials of varying degree of elasticity. For example, the outer surface of the encasement which lies inside the inner opening of the complex core may be characterized by an ordinary elasticity or may be at least partially stiff, and the remaining material of the encasement may have much greater elasticity, so that after the core is put on the nerve the encasement is compressed radially while maintaining approximately the optimum shape of the surface in contact with the nerve. A similar effect may be achieved using thin-walled elastic chambers inside the encasement, which may be filled with air or another gas under pressure. These elastic chambers may be arranged in such a way that their deformation does not change the shape of a portion of the outer surface of the encasement that is adjacent to the nerve.

The use of the complex core that is put on a nerve as shown in FIG. 11 and FIG. 13 allows for a selective affection on the chosen nerve without affecting the adjacent nerves. Due to the homogeneity of the current induced in the opening of the complex core the strength of affection is approximately insensitive to a displacement or a rotation of the complex core in relation to the nerve. This does not exclude fixing the implant inside the body utilizing methods known from the state of the art, for example by the means of surgical anchors fixed by sutures, which significantly restrict or prevent the movement of the complex core, the cable, the power-control system and other elements of the system according to the invention. In some variants on the surface of these elements there are through hole fixing openings 18, that allow for threading of the surgical sutures in order to sew them to durable connective tissues. The complex cores may be used inside the body in any location, for example in the central or peripheral nervous system, to affect spinal nerves or nerves of the limbs, allowing to block nerve impulses within a selected nerve or its branches and enabling to precisely define the area of affection, as shown in FIG. 13. Due to necessity to ensure biocompatibility all elements of the device in contact with the body fluids should comply with the relevant standards. The surface of the complex core, the cable, the power-control system and other elements of the device according to the invention in contact with the body may be also coated utilizing methods known from the state of the art, for example they may be coated with therapeutic substances or other substances that will improve the response of the organism to the implant.

An important advantage of the system according to the invention is the possibility to obtain a complex core having small dimensions due to strong homogeneous magnetization of the component cores, particularly in the case of the component cores arranged along the radius of the complex core, which facilitates the use as an implant. For a further reduction in size of the complex core the component cores may be positioned close to each other or touch each other, wherein the windings of the component cores are preferably concentrated in a small area so that only in that area the distance between the component cores is greater to provide a sufficient space for the windings. For even denser packaging the component cores may touch each other along their entire surface, wherein the windings and the wires may be guided in the grooves made in the component cores. In case of the component cores that touch each other in this way it is preferable if their contact area is characterized by as large air gap as possible, which is larger than 100 μm in the preferred variant, due to the fact that in this case the magnetic field is essentially confined within the volume of each of the component cores, which enables to obtain good homogeneity of magnetization, for example one that is shown in FIG. 6 with a thick line. Such an arrangement is particularly advantageous in case of affecting the dorsal root of spinal nerve as shown in FIG. 11, where due to the small dimensions of the complex core and the anatomical opening in the dura mater it is possible to put the complex core into a small space between the spinal roots without cutting the dura mater. The small dimensions of the complex core also allow for implantation utilizing minimally invasive methods.

In some embodiments of the system according to the invention the complex core may be put near the nerve. In some variants the complex core affects a nerve by the means of the membrane 14, which surrounds the nerve that is affected as shown in FIG. 13 and directs the current induced by the complex core through the membrane openings 15. Such a placement is particularly advantageous when the available space in the vicinity of the affected nerve is limited. The membrane may comprise branches and may surround more than a single nerve. The branches of the membrane may be also connected to other complex cores, which enables to increase the strength of affection on the nerves. In some variants the membranes of the complex cores are connected together and comprise shared membrane openings 15, wherein the complex cores are placed on different sides of a nerve, which increases the homogeneity of the current that affects the nerve. The membrane may be connected to the complex core from both sides at once, it may also comprise inside channels that allow to create more than one passage for the flow of current in the membrane. The possibility of connecting the complex cores 1, the membranes 14 and the membrane openings 15 in complex networks enables to create arbitrarily chosen current flow paths. In some embodiments the membrane 14 may comprise the membrane openings 15 in an arbitrary location, in particular the membrane openings 15 may be arbitrarily placed in the portion of the membrane 14 that is wound around a nerve. In case of the complex core that is put near a nerve the membrane 14 may be short, and the membrane openings 15 may fill most of the portion of the membrane 14 that is wound around the nerve.

The membrane is usually made from elastic materials, which enables to obtain a tight contact with the nerve that is affected. In some variants the membrane may be made from less elastic materials, wherein in order to provide a tight contact with the nerve there may be a membrane seal in the portion of the membrane that is wound around the nerve which acts similarly to the seal 9 of the encasement. In particular, the membrane seal may provide the continuity of the flow of body fluids similarly to the seal 9 of the encasement, for example by the means of a labyrinth seal. In order to ensure the homogeneity of the induced current it is preferable to shape the surface of the membrane, the membrane openings and the membrane seal in such a way, that they have radii of curvature that are as large as possible.

To ensure that as much as possible of the current that flows through the inner opening of the complex core affects the nerve by flowing out through the membrane openings, the surface of the membrane should be tight, while ensuring that it is easy to put on the nerve. For example, the membrane in the shape of a hollow truncated cone may comprise a strap that protrudes from the smaller cone opening, which may be wrapped around the nerve and then inserted into the interior of the membrane through the smaller cone opening. This strap may be then sealed so that the membrane is tight by the sealing band 19 in the form of an elastic band or a bandage, as shown in FIG. 13. The sealing of the membrane after it is put on a nerve may be also obtained by the means of other methods known from the state of the art, for example by gluing. The membrane may be also separably connected to the complex core by the means of a sealing rim made on the surface of the encasement or by the means of the membrane connector 16. In some embodiments the membrane may comprise a stiff shaping element placed inside or outside the membrane that takes shape of a cone or a cylinder, which enables insertion of the membrane in the space between adjacent vertebrae by the means of a surgical technique that resembles the insertion of a spinal cord stimulator. The insertion in the space between adjacent vertebrae may be also achieved by the means of the stiff electric field shaping element 10 shaped like a hollow cone or a cylinder. This enables to create an arbitrary flow of current utilizing one or more complex cores whose membranes or electric field shaping elements are precisely located in the space between adjacent vertebrae in order to affect the dorsal horns of the spinal cord by the means of the current flowing through their openings. The use of the stiff electric field shaping element also enables to get through other obstacles in the body and allows for placing the complex core in a convenient location.

In some cases it is possible to affect the body without immersion in the conducting medium, which allows for a mobile therapy. This goal may be achieved by the means of the gel slab 20 that is touching the surface of the body, creating a closed path for the flow of current around the complex core, as shown in FIG. 14. In this variant the complex core may be also put on the gel slab. In the preferred variant the gel slab behaves like an elastic solid body, which allows for a good contact with the surface of the body. For example, the gel slab may be made from an agar with a mass concentration from 0.5% to 5%, in the preferred variant from 2% to 3%, wherein the mass concentration of sodium chloride ranges from 0.5% to 10%, in the preferred variant from 1% to 3%. It is also possible to utilize the gel slabs made from other gels known from the state of the art, as long as the ion concentration in these gels provides sufficient electrical conductivity. Due to a low concentration of the gelling agents the electrical conductance of a gel is usually close to the electrical conductance of the solution on the basis of which it was prepared. Preferably the gel slab has a low mass, which increases the wearing comfort. This goal may be reached utilizing a high concentration of ions in the gel, which allows for a small electrical resistance in spite of a small cross-sectional area of the gel slab.

It is particularly advantageous to use a gel in which the phenomenon of syneresis occurs. The spontaneous expulsion of a liquid from the gel slab provides an excellent electrical contact with the surface of the body, since the expelled electrically conductive liquid fills all of its unevennesses. An example of such a gel is an agar. In order to prevent the gel slab from drying out, it is advisable to store it before use in a closed container, for example one made from a plastic film. In case of the gel of a biological origin it is preferable to use methods known from the state of the art, such as preservatives or appropriate storage methods, that will prevent the development of microorganisms in the gel slab.

In the preferred variant the gel slab is shaped so that it can be placed on the complex core with ease, which also enables to support it on the core, as shown in FIG. 14. The gel slab may be shaped by the means of stiffening elements, for example the upper surface of the gel slab may be furnished with a thin-walled cover made from stiffer material, that is connected to the gel slab by the means of methods known from the state of the art, for example with the use of protrusions and hooks inserted inside the gel. In another variant the lateral surface of the gel slab has cavities, so that the shape of the gel slab resembles an I-beam, and the stiffening element shaped similarly to the letter $\Omega$ fills these cavities and clamps the gel slab with its arms. In this case the preferred method of production is pouring the stiffening elements situated inside a shaping form with the gel in a liquid state, for example after a heating. In some variants the thin-walled stiffening element is partially pliable, allowing for a partial bend of the stiffened portion of the gel slab.

In the preferred variant the surface of the gel slab that touches the surface of the body is not stiffened, which allows for a good match. In order to improve the bending durability and to avoid an excessive increase of the density of the current it is preferable to provide sufficiently large radii of curvature on the whole surface of the gel slab, for example by rounding its edges. In order to increase the limpness of the gel slab it is also possible to utilize several thin sheets of gel placed one on top of the other instead of a single, uniform gel slab. Such a placement is particularly advantageous when the phenomenon of syneresis occurs, since then the gel slab made from many sheets of gel has almost the same total resistance as a uniform gel slab having the same dimensions. The increase of the gel slab durability may be also achieved by the means of nets made from a fabric that is resistant to stretching placed inside the gel slab. For example, these nets may be made from a cotton or a silicone. The gel slab may be characterized by a variable cross section, for example the portion in contact with the complex core may be thicker than the portion in contact with the body. In order to provide a good electrical contact with the body it is preferable to press the gel slab to the surface of the body. This goal may be achieved utilizing methods known from the state of the art, for example by the means of the elastic fixing band 21 in the form of an elastic band, an adjustable belt or a bandage, which allows to simultaneously fix the gel slab and the complex core, so that they may be worn freely during the therapy, for example on an arm or a leg. In this variant it is particularly advantageous to use the power-control system that is embedded in the complex core so that the whole system is placed inside the fixing band 21, thus improving the mobility of the device. The fixing band 21 may comprise an opening through which the complex core may protrude, which facilitates the fixing in case of the complex core that is not elastic.

In the preferred variant the outer surface of the encasement 3 is a torus inside which at least two component cores 2 are situated, as shown in FIG. 1 and FIG. 2a. This definition should be understood in a broad sense, in particular the torus may also mean objects that are topologically equivalent to a torus. For example, the encasement may have a variable cross section with appendages in the form of the seals 9, it may be nonaxisymmetric, and the inner opening may contain bends and may, in particular, take the shape of an angle bar or a C-channel. Although in the preferred embodiment the torus consists of a single opening, this does not exclude an embodiment wherein the encasement also comprises through hole channels. In the preferred embodiment the component cores 2 should encircle the opening of the torus so that they induce the emf in the conducting medium 7. For example, in case of the torus-shaped component cores 2 that encircle the opening of the torus-shaped encasement 3 and are located inside the encasement, the magnetic flux through a surface, whose boundary is a loop that passes through the opening of the encasement and encircles it inside the conducting medium, is a sum of magnetic fluxes generated in the cross section of each of the component cores, therefore the total emf along the loop is a sum of the electromotive forces generated by the component cores. For this reason, the charges inside the conducting medium will experience an emf along said loop which will generate the flow of current around it and around the encasement Similar reasoning may be used to establish, if the component cores of different shapes and placement inside the encasement may create a continuous flow of current inside the conducting medium. For example, for torus-shaped component cores 2 situated inside the encasement that do not encircle its opening, the emf along said loop is equal to zero, and there is no continuous flow of current inside the conducting medium provided that the encasement is an ideal insulator.

The system according to the invention enables to obtain a high intensity and gradient of the electric field E inside the patient's body, which is necessary in order to achieve the effect of a nerve impulse block without the risk involved in methods that utilize electrodes. It is known that in an electrode the charge carriers are electrons, whereas in conductive fluids, such as electrolytes, the charge carriers are ions. Due to the fact that the ions may not enter inside the electrode, the flow of current is sustained by a chemical reaction that occurs on its surface, wherein there is an exchange of charges with the electrode combined with creation of products of reduction and oxidation reactions. In case of an electrode put near the human body the newly created chemical compounds may lead to a severe skin irritation. In case of the water as the conducting medium a voltage that is higher than approximately 1.23 V causes an irreversible electrolysis, which creates hydrogen and hydroxide ions resulting in, respectively, a decrease and increase of the solution's pH. Due to the fact that in order to obtain the effect of a nerve impulse block high voltages are required, the creation of irritant substances is impossible to avoid for the electrodes, and the irreversibility of the electrolysis results in irritations occurring also in case of the quickly changing or electrically balanced time courses. Another problem related to the electrolysis is the creation of gas-filled bubbles that gradually reduce the surface of the electrode in the electrical contact with the medium, leading to a local increase of the electric current density that may in extreme cases cause burns. Taking into account the limitations of the methods utilizing electrodes there is a need for a system for affecting nerve fibers that ensures patient safety. In the system according to the invention the electric field is generated by the complex core in space, therefore the current creates closed loops that do not encounter discontinuities in the form of electrodes on their path, as shown in FIG. 2b and FIG. 8. The system according to the invention is insensitive to unequal distance from the skin and the change of radius of curvature of the electrode on edges, which lead locally to a significant increase of current density that causes burns. For a patient this means that there is no need for hair removal in the place that is intended to be affected by the electric field, and there is a possibility of an arbitrary movement of the core while the power-control system is active in order to find the place, where affecting the nerves is most beneficial.

Another advantage resulting from the use of the system according to the invention is the possibility to utilize lower supply voltage compared to the voltage required when the electrodes are used, wherein a large part of the electric field intensity is lost in the electrical double layer and does not affect the body. This phenomenon is particularly severe for impulses in the order of tens of microseconds and longer, wherein the electric field intensity gradually approaches zero with time. This effect does not occur in the system according to the invention, which enables to affect the nerves by the electric field in the range defined by the time period in the order of tens and hundreds of microseconds, milliseconds, or longer, with the use of a small voltage.

In the preferred variant of the system the conducting medium is a water with salt in physiological concentration, therefore from the viewpoint of the ions the patient's body and the medium constitute an electrical unity, through which they may move freely, so that the chemical reactions are not initiated. This does not exclude a variant, wherein the conducting medium has a lower or higher conductivity than the saline, it is important that the electric current has the ability to move freely. It should be emphasized that the human body is divided into cells surrounded by membranes which create a barrier for the current flow, although due to a small thickness, in the order of a dozen or so nanometers, these membranes are characterized by a very high electrical capacitance, resulting in an ability to store a large charge with a small rise of the voltage. From the viewpoint of the ions the membranes do not influence the current flow significantly, due to the fact that they are capable of storing a large amount of charge which is embedded during the impulse without generating a considerable electric field that would hamper the further flow of the ions. The stored charge is freed during the change of the direction of the electric field, therefore the membrane potential changes periodically and oscillates between determined maximum values.

The system according to the invention generates an electromagnetic field in the conducting medium and in the body, which affects nerve fibers by the change of the membrane potential of the nerve cells that is caused by the flow of the current and the resulting change of conductance of the voltage-gated ion channels. In the preferred embodiment the cores take shape of closed loops, therefore the magnetic field is essentially confined within their volume, and the majority of the observed effects is caused by the electric field. The changes of the membrane potential usually depend on the electric field gradient, and in the case of affecting an end of a nerve fiber or a bend of a nerve the dominant factor is the value of the electric field intensity. For this reason it is particularly advantageous to utilize the component cores placed along the radius of the complex core, which allows to efficiently obtain a high intensity and gradient of the electric field that affects the nerve fibers. This allows to obtain a similar membrane potential of all of the nerve fibers inside the affected nerve, since due to high intensity and gradient of the electric field the steady state of the flow of the current may be reached quickly, and the electrical properties of the conducting medium in the vicinity of the nerve fibers are similar. It is particularly advantageous if the emf has a small value so that the membrane potential in the steady state is around the minimum value that is required in order to obtain the desired strength of affection. Depending on the chosen time course of the electric current the change of the membrane potential may cause an initiation or block of an action potential as well as a change to the dynamics of the response of the nerve to the coming impulses. It should be emphasized that the flow of current generated by the cores is balanced, and the total current intensity approaches zero, which follows from the Faraday's law. According to the scientific literature a block of nerve fibers may be obtained using a changing current flow of sufficiently high intensity. It should be noted that no specific time course of the current is required and the change of the intensity does not have to be periodical and may differ in each cycle. The numerical simulations of the nerve behavior by the means of the Hodgkin-Huxley equations demonstrate that due to the strongly nonlinear nature of a nerve fiber the block may be obtained in a variety of ways, provided that the current has a sufficiently high intensity. Based on the results of the computer simulations it may be concluded that the block is caused by an electric "freezing" of the nerve during its attempt to return to the state in which it is able to receive the next action potential. The inactivation gate of the sodium channel remains in a partially closed state, while the potassium channels are partially opened, which results respectively in a difficulty to increase the membrane potential due to a block of the flow of the sodium ions inside the cell and a further decrease of the membrane potential caused by an outflow of the potassium ions. In the case of the current of a higher intensity a transgression of the equilibrium potential of the sodium channels that equals approximately 60 mV by the membrane is of high importance, as this causes an outflow of the sodium ions outside the cell despite the high membrane potential, which allows for an effective hyperpolarization of the nerve fiber. This has also a stabilizing effect, as due to the very high conductance of the sodium channels it significantly reduces a further increase of the potential of the cell membrane, thus allowing to reach the block of the action potential in the nerve fibers of different sizes at the same time.

It should be emphasized that in spite of the fact that the cell membrane potential in the affected location may change considerably with time, the total voltage is close to the resting potential or lower, therefore these changes do not usually cause an initiation of the action potential and do not propagate to the neighboring nodes of Ranvier. The affection of the system on the nerve fibers may also cause effects that persist for a certain time after the direct affection is ceased, which is particularly advantageous in the case of the pain therapy. For example, as a result of the affection there may be a change of concentration of the sodium and potassium ions or other elements that are present inside the cell, resulting in a change of the resting potential and a change of the equilibrium potential of the individual ions. Although the balance will be eventually restored by the means of the sodium-potassium pump or by other systems that transport the ions, the resulting changes may block or hamper the propagation of the action potential. The blocking effect may be significantly prolonged if, due to the continuous strive to restore the balance, the ion transport systems depleted locally stored energy resources, resulting in a prolongation of the duration of the block by the time needed to transport the resources along the nerve fiber.

According to the scientific literature affecting the nerve fibers by the electric field may also activate an endogenous pain inhibition mechanism, such as an opioid secretion. This effect may impact the perception of the pain not only in the place that is affected by the device, but also in the whole body. Due to the fact that the analgesia may be sustained for a long time this effect may be particularly advantageous in order to reduce the pain in places that are hard to reach.

An important factor that influences the effectiveness of the nerve impulse block is the size of the area, in which the cell membrane potential has a sufficiently high value in order to reach the desired effect. For example, in a situation when the utilized current intensity allows only to obtain a partial block, and the affected area has a size larger than several millimeters, the action potential must propagate through many nodes of Ranvier, which significantly increases the chance to block the nerve impulse. For this reason it is preferable to form the area of the electric field which is capable of blocking the action potential that is as large as possible. Such a result may be obtained effectively by adapting the shape of the core to the nerve course, for example by placing the elongated complex core 1 along the nerve, analogously to the placement shown in FIG. 10.

Although the use of the system to provide the analgesia is particularly advantageous, this does not exclude other medical applications involving a flow of ions in the body that are known in the literature. As an example, the system according to the invention may be used to treat osteoarthritis, in an anti-inflammatory treatment, in a treatment of cardiovascular disorders, to stimulate regeneration of tissues, to stimulate muscles and to soften scars. The use of the time courses of the induced current in the form of separate impulses may be utilized to stimulate motor and sensory nerves. The possibility of blocking motor nerves resulting in a relaxation of the muscles may be used in the therapy of many neurological disorders, for example in the case of Parkinson's and Huntington's disease, and to treat dystonia and spasticity. The conducting medium 7 may also comprise therapeutic substances that are to be introduced into the organism through the skin. The system according to the invention may be also used to generate the flow of the ions in the conducting medium wherever it has a technical justification, for example to measure the resistance of the object situated in the medium inside the complex core 1 and sealed by the encasement 3, wherein one of the component cores 2 is intended to induce the electric field in the medium, and second component core is a current transformer. The term inside the complex core that was used to describe the method to measure the resistance of an object should be in this case interpreted exceptionally as meaning that the object is situated at least partially inside the inner opening of the complex core. Another application of the system according to the invention is the use of the complex core with the stiff encasement without the seals and the component cores placed along its radius as an compact and efficient transformer for general use. In this example, the complex core may be situated in the air, and the affected object may be some outside electric wire that passes through the inner opening of the complex core, so that a voltage difference is induced at the ends of this wire.

An important feature of the invention is a high efficiency, which enables to utilize a battery power supply. An experiment has shown that the system described in the example No. 1 which was powered with four lithium-ion batteries type 18650 worked for over an hour. Due to the fact, that the losses are related to the total magnetic energy of the system, in case of the significantly smaller complex cores utilized as implants, whose dimensions are decreased to put them directly on a nerve so that the resistance along the loop of the induced current is small, the anticipated working time of the system may reach hundreds of days. In order to obtain the high efficiency in the preferred embodiment litz wires are utilized, which protect from an adverse influence of the skin effect. The surface of the wires that is insulated with a lacquer creates an additional security against an electrical breakdown. It is also important to utilize wires of sufficiently large cross section area in order to obtain small conduction losses and to provide sufficiently high value of the time constant for the each of the cores. The power-control systems creates and controls the changing current flowing through the wires 6 and the windings 5 of the component cores 2, which creates and controls the flow of the induced current in the conducting medium. In the preferred embodiment the power-control system controls the current flow through the complex cores by the means of MOSFET type transistors that are connected in a H bridge configuration. This does not exclude an embodiment, wherein a half-H bridge or other electronic circuit topology that is known from the state of the art is utilized. In order to reduce the losses it is particularly important to utilize transistors having low resistance and low gate capacitance, which allows for lower switching losses. It is also important to minimize the parasitic inductance of the wires and traces on the board, due to the fact that the quickly changing currents utilized in the system may generate high voltage losses. For this reason in the preferred embodiment the input and output current traces that are connected with the wires 6 are situated as close as possible to each other. The power-control system made in this way allows to retrieve to the supply capacitor a large part of the energy utilized to temporarily magnetize the cores in each cycle, which considerably reduces the system energy consumption. In order to obtain the high efficiency it is also important to lower the losses inside the core itself, which result from eddy currents and the shape of the hysteresis loop of the utilized magnetic material.

In some embodiments of the invention it is possible to change the number and type of the complex cores that are connected to the device. This allows for an adjustment to the shape of various body parts in order to obtain the optimum results. The possibility of attaching and detaching the complex cores during the surgery also facilitates the implantation of the complex cores and the power-control system inside the body. The connection of the cables 4, which lead to the complex cores 1, may be obtained by the means of watertight connectors with the methods known in the state of the art. It is also possible to utilize an induction power supply, in which the end of the wire 6 comprises a fastener that allows to create a closed loop around an intermediary core which is powered directly by the power-control system. The changing magnetization generated by the power-control system in the intermediary core causes a changing flow of current in the wire 6 and the winding 5, thus inducing the emf in the component core 2. It is also possible to utilize a similar system, in which the wire 5 ends near the power-control system with a coil that is put near a coil that is powered directly by the power-control system, thus enabling to obtain a wireless power supply by the means of the electromagnetic induction phenomenon. The use of the galvanic isolation provides an additional security, which is particularly advantageous when there are dangerously high voltages in the power-control system. This embodiment also allows to ensure a complete watertightness.

Although the use of the battery power supply is preferred due to convenience and safety of the user, this does not exclude an embodiment, wherein the electric energy of the power-control system is supplied directly by the mains voltage, provided that the watertightness of all connections is ensured. A solution that is more preferred for safety reasons is the use of the wireless power supply by the means of coils, that allows to ensure a complete watertightness. This is particularly advantageous in case of the complex core and the power-control system implanted inside the body, wherein the power-control system may be powered by the means of the wireless power supply and controlled transcutaneously similarly to a cochlear implant, which enables to extend the working time of the system. It is also possible to supply the energy to the power-control system inductively with the use of the intermediary core in a similar way to the already described induction power supply of the component core. This power supply may be used to deliver the energy to the power-control system during work or to charge the batteries.

The use of the mains supply ensures a constant electromotive force generated by the complex core, which in the case of the battery power supply may change somewhat as the battery gradually reaches its cut-off voltage. This effect may be balanced by a suitable change of the time period and incidence of the impulses. In some embodiments of the power supply system, wherein the batteries are used as a source of the electric energy, the constant amplitude of the impulses is provided by a voltage converter that is built into the power-control system. The voltage converter may be also utilized in order to control the strength of affection by changing the induced electric field.

The power-control system may be controlled directly by a patient or by a person that manages the therapy by the means of methods described in the state of the art. For example, it can be done by a wired or wireless remote or a touchscreen. The control may involve all or some of the important device work parameters, such as the turning the device on and off, the amplitude, the frequency, the type of the impulse and the time to reach the target parameters as well as other settings. The cover of the power-control system may comprise handles, enabling it to hang on the edge of a vessel with the conducting medium, allowing for a convenient access to the touchscreen for the user. In the case when the device is used under full submersion the power-control system may be made in such a way that it floats on the surface of the water in a stable position, thus facilitating the access to the control panel. In some embodiments the power-control system is placed near the complex core 1, for example by at least partial building into the encasement 3. In case of using the complex core as an implant the power-control system and other elements of the system according to the invention may be implanted inside the body utilizing methods known from the state of the art so that their placement is comfortable for the patient. The outer cover of the power-control system may also have an additional function due to the use of suitable stiff materials, for example it may act as an interspinous process device which may decrease the number of implants placed inside the body.

In one of the variants the complex core 1 affects the nerve fibers by being put near the patient in such a way, that the inside of the core does not encompass any part of the body, as shown in FIG. 10. This means that the inner opening of the complex core does not encompass any part of the body. The complex core may be situated at some distance from the body or, in the preferred variant, it may touch it completely or partially, which reduces the losses caused by the current flowing around the core that does not enter the body. In the described variant the cores enable to affect any part of the body, in particular the limbs, the face, the neck and the nerve roots. It is particularly advantageous to use this variant for transcranial stimulation. In order to facilitate the positioning the complex core 1 may be furnished with elastic bands 17 with a tightening mechanism that is known from the state of the art, for example one that utilizes a fixing with a belt and a buckle. The use of the elastic core enables to change the shape of the area affected by the electric field, allowing to choose the nerves that are affected.

In the next variant the inside of the complex core 1 encompasses the patient's body, as shown in FIG. 4. This means that the inner opening of the complex core encompasses a part of the body. In this case the complex core 1 is put on the forearm. The core may be situated at some distance from the body or, in the preferred variant, it may touch it completely or partially. In the preferred variant the inner opening of the core is formed in such a way that the core may be put on with ease, which can be accomplished, in particular, by utilizing an opening in the shape of a cylinder. The use of the elastic core enables to obtain a tight contact with the skin, which significantly increases the electric field intensity that affects the nerve fibers. In the described variant the cores may encompass the limbs, the head, the neck, the waist, the torso or other parts of the body. In some variants the system for inducing an electric field according to the invention is characterized by the ability to use the same complex core as a core that does or does not encompass the patient's body, whereby the complex core advantageously has an ability to be connected with the electric field shaping element 10 or the membrane 14, which allow to optimally shape the electric field lines in order to affect various body parts.

In some variants the conducting medium 7 is an electrolyte in the form of a gel, for example it may be an agar comprising a salt. In this embodiment the system according to the invention may be used without immersion in the water-filled vessel, for example in the variant shown in FIG. 10 or FIG. 4 the gel may be deposited around the complex core 1 and the affected area of the body, to provide a continuous flow of the current. It is also possible to utilize membranes that seal a portion of the body and encompass the complex core, which enable to fill the inside of the membrane and hamper an outflow of the gel if it does not have a sufficient viscosity.

The affection of the device on the nervous system depends on the change of the membrane potential of a nerve fiber, so it depends on the amount of the charge that is displaced in a given moment. For this reason the strength of the affection of the system according to the invention may be changed by an increase of the electric field amplitude, by an increase of the time period or by a change of the time course. Due to the fact that the system of resistors and capacitors that may be used in order to numerically approximate the electrical conduction of a nerve creates a low-pass filter, in case of time courses of the current having a frequency that is higher than the cutoff frequency, the increase of the strength of affection by the means of the increase of the electric field intensity may be more efficient than the increase of the time period, which is true for lower frequencies. The experience shows that it is desirable to gradually increase the strength of the affection of the system on the patient, which allows to comfortably adjust to the new conditions. In the preferred embodiment the time to reach the target parameters may be delayed in the range from single seconds to tens of minutes. For example, the time period may have an initial value of 20 μs and may grow at a pace of 20 μs per minute to a final value of 300 μs. The slow change of the time course of the induced current enables to avoid an unwanted excitation of the nerve fibers.

The system according to the invention may be used to affect the body by the electric field having an arbitrary time course that is possible to obtain in agreement with the Faraday's law, which means that the time course of the current is balanced in time. In particular, the power-control system may induce an emf having a sinusoidal, a triangle, a pulse or a rectangular time course with various duty cycles, as well as the modifications of these time courses resulting from holding the value of the emf at a constant level for some time.

The response of the nervous system may be particularly prominent for certain time courses of the current, for example those characterized by a specific frequency. This advantageously gives an ability to selectively block a certain type of the nerve fibers, for example motor or sensory. If it is desirable to achieve a full block of the action potential the emf of the core may be induced by a current whose time course is a sum of the time courses having different amplitudes and frequencies. This time course may be generated directly by the power-control system or indirectly by the sum of the emf originating from the independently powered component cores 2 in the conducting medium, wherein each component core may generate an emf of different amplitude, frequency or phase. This system may be easier to implement due to the simplicity of the power-control system design. The possibility of utilizing only some of the component cores also allows to control the strength of affection.

The system according to the invention requires a partial or a full immersion of the affected area in the conducting medium 7, which should be non-irritant for the skin. The increase of the conductivity of the medium is advantageous and allows to increase the current affecting the nerve with the same electric field intensity. In the preferred embodiment the conducting medium 7 is an aqueous salt solution, for example a solution of potassium chloride or sodium chloride, from trace amounts to saturation of the solution, although this does not exclude the use of other conducting fluid. The temperature of the medium also significantly influences the affection. Preferably, a warm bath adjusted so that it would be pleasant for the patient is used, since the electric conductivity of the ion-containing solutions increases significantly with the temperature.

A key feature of the invention is the assurance of the safety of using the system also during the immersion of the patient in a vessel with the conducting medium, such as a bathtub, a pool, a lake or a sea. In some variants due to the use of the tight connections between the complex cores 1, the cable 4 and the power-control system the ensemble may be used by a patient in a full immersion. The safety is above all the result of the use of a low voltage in the power-control system and the application of the complex core in order to obtain a sufficiently high intensity of the induced electric field. It is the high voltage that poses a potential threat in case of a damage to the securities, such as the outer insulation of the winding 5, the wire 6 and the cable 4, due to the fact that it may cause an uncontrolled flow of the current through the patient's body. The reduction of the highest voltage of the wires 6 to the level of 12 V, in the preferred variant lower than 10 V, in a more preferred variant lower than 5 V and in the most preferred variant lower than 3 V enables to limit this current to a safe level. Due to the fact that the power-control system in the preferred embodiment is completely isolated from the surroundings, if the insulation is interrupted the current will not flow continuously, the only flow will be a temporary capacitance current of a small intensity, whose value is also significantly limited by the use of the low voltage and by a potentially small area of the exposed conductor in the place where the insulation is broken. In the preferred embodiment the interruption of the insulation will be instantaneously detected by a residual-current device security which compares the output and input current that flows to the system through the wires 6 by the means of a current transformer. If a difference in the balance of the current is detected the power supply will be immediately cut off, preventing further flow of the current. The increased security also results from the fact that the electric field is generated by changes of current flow through the core, wherein the maximum total electric charge that may be displaced by the core depends on its size and the value of the saturation magnetization and may not be increased, also due to an accident. A potential failure of the power-control system that leads to a short-circuit will not generate a significant electric field in the medium after the state of the magnetic saturation is reached in a component core, therefore it would not impact the security. A short-circuit may be detected and stopped with ease by the power-control system utilizing sensors that monitor the temperature of the wires, it may be also interrupted automatically by the means of a fuse.

It should be emphasized that although the described threats are events of very low probability, it is highly desirable to have additional safeguards to mitigate their effects. For further protection of the system the preferred embodiment utilizes methods known from the art, such as the multiple insulation of the windings 5, the wires 6 and the cable 4, that is resistant to mechanical damage, and a shielding from a wire connected to a fixed potential placed inside the cable 4 close to its surface, which creates an internal short-circuit in the system when the insulation is interrupted, that may be immediately detected and stopped. All the connections should be sealed in order to secure against ingress of the conducting medium to the system and should comply at least with the IP65 standard, and in the preferred embodiment with the IP68 standard or a better one, which allows the system to be used in full immersion.

In order to minimize the risk to the patient resulting from the possibility of an unintentional affection on the nerve fibers which may, for example, have an effect on the functioning of the heart, in case of the use of the system in full immersion it is preferable to use a protective suit made from an electrically non-conductive material. This suit should cover the chest area. In the preferred embodiment the protective suit may comprise an opening, which enables to affect the patient's back by the electric field. In case of using a system which was designed to generate very high intensity of the electric field, that is capable of affecting the nerves in the spinal cord, the suit may also cover the cervical vertebrae, other vertebrae which are to be protected from the affection and the vagus nerve. Materials with good insulation properties, that are elastic and resistant to mechanical damage such as a silicone or a rubber are preferred. Due to the well defined area of affection of the core, covering the body in the vicinity of the nerve allows to eliminate the risk of an accidental affection. It should be emphasized that this is only a safeguard measure that is intended as an additional security. The basis for the safe use of the device is the user's knowledge of the permitted area of affection on the nerve fibers. In many cases the use of the protective suit may be unnecessary. This is the case when the nerve fibers that have an effect on the functioning of the heart are not immersed in the conducting medium, for example when immersed from the waist down, when only the patient's back is immersed with a suitably chosen intensity of the electric field, and when only the face or the limbs are immersed.

The effects of the affection of the system according to the invention change significantly depending on the chosen frequency, the time course and the intensity of the electric field. All experiments were carried out with the use of the windings 5 and the wires 6 surrounded by at least a single layer of insulation having a thickness of at least 0.5 mm, and with the use of the cable 4 with an internal shielding braid connected to a fixed potential of the power-control system, which excludes the influence of capacitance effects on the observed results.

For a current of a rectangular time course with a duty cycle of 0.5 and a time period equal to 30 µs, after the complex core is put on the wrist that is immersed in the conducting medium, as the electric field intensity increases, the block of the motor nerves appears first, manifested in inability to move the fingers of the hand. The further increase of the emf causes the block of the sensory nerves with a discernible loss of the feeling of the touch on the skin of the hand. During a rapid growth of the strength of the affection muscle contractions may appear, which stop spontaneously after some time. The contraction of the muscles may be avoided by a proper choice of the control parameters, by the use of a slow increase of the strength of the affection on the nerve or by the use of a lower frequency of the time course of the current. After a few minutes of affection the skin of the fingers ceases to feel the acute pain caused by a needle stick. When the strength and the duration of affection are sufficiently large, which usually amounts to approximately 15 minutes, the effect of the reduced susceptibility to stimuli lasts for a few hours after the completion of the treatment, after which the original state is restored without any discernible changes.

The effects analogous to those described above are also obtained for time courses of a constant emf when the strength of the affection is augmented by the increase of the time period of the time course. In order to verify if the obtained effect may be relevant for the therapy of pain the author carried out on himself a standard laboratory test that entailed the injection of the saline comprising 0.2% formalin, which, according to the literature, causes a strong stimulation of the nerve fibers that are responsible for acute and chronic pain. The author's experience shows that the injection of the formalin causes very strong pain, that is hard to withstand without any movement and resembles the sting of a wasp, which gradually decreases, changing after a minute into a highly irritating but easier to bear subsequent pain that lasts for a few minutes. In the case of the tests that entailed multiple subcutaneous injections of 125 µl of the formalin solution into various places on the body, that had been previously affected by the electric field for a long time with the system according to the invention, the strong initial pain was significantly reduced, becoming barely perceptible and acceptable, and the subsequent pain became completely imperceptible. Comparing the pain perception after the injection of the formalin into a place that was previously affected for a long time and into a place not affected by the device one may notice a strong analgesia in the place that was previously affected, although a partial pain reduction in the whole body is also perceptible, which suggests activity of the central pain control system by the means of the opioid secretion. In some of the tests the analgesia was so strong that no perception of the pain caused by the formalin in the place that was previously affected for a long time could be perceived also several dozens of minutes after the completion of the therapy. Such a strong local effect may be caused by the action of the peripheral opioid receptors in the C fibers. In some of the experiments the long lasting analgesic effect caused by the opioid secretion might have been amplified by the affection of the system according to the invention on the dorsal horns of the spinal cord during immersion in a bathtub.

Example No. 1

The experiment utilized the complex core 1 comprising three ferrite component cores 2 having the cross section of 22×19 mm and the inner diameter of 80 mm that were tightly assembled together by the means of the tight insulating encasement 3 as shown in FIG. 7, with the electric field shaping element 10 detached. The use of the elastic encasement 3 furnished with the seals 9 in the form of the flaps made from a plastic film enabled to seal the space between the complex core and the body and to eliminate the clearance. Each component core was wound with a single turn, wherein the windings were connected in parallel. The power-control system was powered with four lithium-ion batteries type 18650 connected in parallel and the electromotive force generated by each component core did not exceed 4V. The complex core surrounded the forearm of the left hand in the vicinity of the wrist. The arm together with the complex core was immersed in a bathtub filled with 1% solution of the kitchen salt. The strength of the affection was increased due to the steady change of the time period of the current induced by the cores having a rectangular time course with the duty cycle of 0.5 from 20 µs to 120 µs in one minute, after which the time course having the time period of 120 µs affected the body for the next 15 minutes. A relatively abrupt increase of the strength of the affection in this case caused brief contractions of the hand. After finishing the affection, 125 µl of 0.2% solution of formalin in the saline were subcutaneously injected several times into the middle finger and the thumb, which, depending on the exact location, caused no pain perception or gave barely perceptible irritation. The analgesic effect did not influence the movement of the fingers. After 30 minutes a subcutaneous injection of the formalin into the left forearm did not cause any pain perception. The injection of the formalin into the same location on the forearm of the right hand was perceptible, although the feeling of pain was weak and easy to bear. The injection of the formalin into the left forearm after 24 hours gave the standard reaction, which is a pain that is strong and hard to bear.

Example No. 2

The experiment utilized the system described in the example No. 1 with the electric field shaping element 10 attached, in which the centrally located opening had an inside diameter equal to 20 mm as shown in FIG. 7. After putting the opening near the body 12 in the vicinity of the inner side of the wrist joint of the left hand that was immersed in a bathtub filled with 1% solution of the kitchen salt it was possible to obtain an immediate and complete loss of the feeling of the touch in the thumb, the forefinger and the middle finger on the inner side of the hand. The block was not accompanied by contractions, pain or a restriction of the finger mobility, and the feeling of the touch returned immediately after the affection by the electric field was ceased.

The presented description of the test results only approximates an exemplary use of the system according to the invention by depicting the effects observed by the author. However, it should be noted that this in no way limits further applications for different parameters of the induced field, other objects and places of affection as well as other variants in agreement with the essence of the invention.

The invention claimed is:

1. A system for inducing an electric field, comprising:
   at least two component cores;
   at least two windings; and
   a torus-shaped encasement having an outer surface that is electrically non-conductive,
   wherein the at least two component cores are independent magnetic circuits,
   wherein each of the at least two component cores is wound around with at least one of the at least two windings,
   wherein each of the at least two windings is configured to pass electric current to change a magnetic flux of one of the at least two component cores, the magnetic flux of one of the at least two component cores being substantially confined within a volume of the one of the at least two component cores,
   wherein the at least two component cores are situated inside a volume enclosed by the outer surface of the encasement,
   wherein the at least two component cores encircle an opening of the encasement, and
   wherein the encasement is configured to be placed inside a conducting medium.

2. The system of claim 1, wherein at least a portion of the outer surface of the encasement is capable of a reversible change of shape by a small force.

3. The system of claim 1, wherein an electrically non-conductive interior of the encasement is configured to surround and fix in place the at least two component cores.

4. The system of claim 1, wherein at least two of the at least two component cores reach saturation magnetization at the same time.

5. The system of claim 1, wherein the electric currents passing through at least two of the at least two windings are distinguished by different time courses.

6. The system of claim 1, wherein the encasement comprises at least one chamber capable of a reversible change of shape by a small pressure, wherein the at least one chamber is configured to be filled with a fluid.

7. The system of claim 1, wherein the encasement comprises at least one electrically non-conductive seal having an ability of bending by a small force.

8. The system of claim 1, further comprising an electrically non-conductive electric field shaping element configured to be situated inside the conducting medium, wherein the electric field shaping element comprises at least one opening, wherein the encasement is configured to be tightly and separably connected to the electric field shaping element, such that when the encasement is connected to the electric field shaping element, and the electric field shaping element is situated inside the conducting medium, a portion of the conducting medium is in a shape of a closed loop passing through the opening of the encasement and the at least one opening of the electric field shaping element, wherein said portion of the conducting medium encircles the encasement and the electric field shaping element.

9. The system of claim 1, further comprising an electrically non-conductive, limp membrane configured to be situated inside the conducting medium, wherein the membrane comprises at least one opening, wherein the encasement is configured to be tightly and separably connected to the membrane, such that when the encasement is connected to the membrane, and the membrane is situated inside the conducting medium, a portion of the conducting medium is in a shape of a closed loop passing through the opening of the encasement and the at least one opening of the membrane, wherein said portion of the conducting medium encircles the encasement and the membrane.

10. The system of claim 1, wherein the system is configured to be formed by joining at least two parts, wherein each of said at least two parts comprises at least a portion of the at least two component cores and at least a portion of the encasement, wherein at least one of said at least two parts comprises at least one of the at least two windings, wherein each of said at least two parts comprises surfaces of interconnection, wherein each said surface of interconnection is configured to be joined with another of said surfaces of interconnection of another part of said at least two parts.

11. The system of claim 10, wherein the surfaces of interconnection of said at least two parts are flat.

12. The system of claim 10, wherein at least two of said at least two parts are configured to be joined by wringing the surfaces of interconnection together.

13. The system of claim 10, wherein at least two of said at least two parts are configured to be joined by a fastener.

14. An implantable system for inducing an electric field, wherein the system is configured to be formed by joining at least two parts, wherein each of said at least two parts comprises surfaces of interconnection, wherein each said surface of interconnection is configured to be joined with another of said surfaces of interconnection of another part of said at least two parts, wherein the system comprises:
   at least two component cores;
   at least two windings; and
   a torus-shaped encasement having an outer surface that is electrically non-conductive,
   wherein each of said at least two parts comprises at least a portion of the at least two component cores and at least a portion of the encasement,
   wherein at least one of said at least two parts comprises at least one of the at least two windings,
   wherein the at least two component cores are independent magnetic circuits,
   wherein each of the at least two component cores is wound around with at least one of the at least two windings,
   wherein each of the at least two windings is configured to pass electric current to change magnetization of at least one of the at least two component cores,
   wherein the at least two component cores are situated inside the encasement,
   wherein the at least two component cores encircle an opening of the encasement,
   wherein the encasement is configured to be placed inside a conducting medium, and
   wherein the system is configured to be placed around a nerve such that said nerve passes through the opening of the encasement.

15. The system of claim 14, wherein at least a portion of the outer surface of the encasement is capable of a reversible change of shape by a small force.

16. The system of claim 14, wherein at least two of the at least two component cores reach saturation magnetization at approximately the same time.

17. The system of claim 14, wherein the surfaces of interconnection of said at least two parts are flat.

18. The system of claim 14, wherein at least two of said at least two parts are configured to be joined by wringing the surfaces of interconnection together.

19. The system of claim 14, wherein at least two of said at least two parts are configured to be joined by a fastener.

20. The system of claim 14, wherein the encasement has a variable radius of curvature along the outer surface such that parts of the encasement, wherein said parts of the encasement, which have a small radius of curvature, are located away from said nerve when the system is placed around said nerve.

21. A system for inducing an electric field, wherein the system is configured to be formed by joining at least two parts, wherein each of said at least two parts comprises surfaces of interconnection, wherein each said surface of interconnection is configured to be joined with another of said surfaces of interconnection of another part of said at least two parts, wherein the system comprises:

one or more component cores;
one or more windings; and
a torus-shaped encasement having an outer surface that is electrically non-conductive,
wherein each of said at least two parts comprises at least a portion of the one or more component cores and at least a portion of the encasement,
wherein at least one of said at least two parts comprises at least one of the one or more windings,
wherein at least two of said at least two parts are joined by wringing the surfaces of interconnection together,
wherein the one or more component cores are independent magnetic circuits,
wherein each of the one or more component cores is wound around with at least one of the one or more windings,
wherein each of the one or more windings is configured to pass electric current to change a magnetic flux of at least one of the one or more component cores, the magnetic flux of at least one of the one or more component cores being substantially confined within a volume of the at least one of the one or more component cores,
wherein the one or more component cores are situated inside the encasement,
wherein the one or more component cores encircle an opening of the encasement, and
wherein the encasement is configured to be placed inside a conducting medium.

* * * * *

UNITED STATES PATENT AND TRADEMARK OFFICE
CERTIFICATE OF CORRECTION

PATENT NO. : 11,559,698 B2
APPLICATION NO. : 17/268537
DATED : January 24, 2023
INVENTOR(S) : Krzysztof Mellem It is certified that error appears in the above-identified patent and that said Letters Patent is hereby corrected as shown below:

In the Claims

In Claim 20, Column 39, Lines 1 and 2, delete "wherein said parts of the encasement,".

Signed and Sealed this
Twenty-eighth Day of February, 2023

Katherine Kelly Vidal
*Director of the United States Patent and Trademark Office*